US009260480B2

(12) United States Patent
Kalita et al.

(10) Patent No.: US 9,260,480 B2
(45) Date of Patent: *Feb. 16, 2016

(54) PROCESS FOR THE MANUFACTURE OF DEGARELIX AND ITS INTERMEDIATES

(75) Inventors: Dipak Kalita, Andhra Pradesh (IN); Mohosin Layek, West Bengal (IN); Atmakuri Venkata Dhanunjaya Rao, Andhra Pradesh (IN); Venkat Aravinda Potula, Andhra Pradesh (IN); Vikas Gajare, Andhra Pradesh (IN); Kesavan Balakumaran, Andhra Pradesh (IN); Anders Nilsson, Lund (SE); Guangcheng Jiang, San Diego, CA (US)

(73) Assignee: Ferring B.V., HHoofddorp (NL)

( * ) Notice: Subject to any disclaimer, the term of this patent is extended or adjusted under 35 U.S.C. 154(b) by 159 days.

This patent is subject to a terminal disclaimer.

(21) Appl. No.: 13/881,751

(22) PCT Filed: Oct. 26, 2011

(86) PCT No.: PCT/EP2011/068733
§ 371 (c)(1),
(2), (4) Date: Jul. 11, 2013

(87) PCT Pub. No.: WO2012/055903
PCT Pub. Date: May 3, 2012

(65) Prior Publication Data
US 2013/0281662 A1    Oct. 24, 2013

(30) Foreign Application Priority Data

Oct. 27, 2010  (EP) .................... 10189011

(51) Int. Cl.
| C07K 7/02 | (2006.01) |
| C07K 7/06 | (2006.01) |
| C07K 7/23 | (2006.01) |
| C07K 7/00 | (2006.01) |
| C07K 7/04 | (2006.01) |
| C07K 1/02 | (2006.01) |
| C07K 1/06 | (2006.01) |
| C07K 1/10 | (2006.01) |
| A61K 38/00 | (2006.01) |
| A61K 38/09 | (2006.01) |
| A61K 38/08 | (2006.01) |
| A61K 38/04 | (2006.01) |
| C07K 5/08 | (2006.01) |

(52) U.S. Cl.
CPC . *C07K 7/06* (2013.01); *A61K 38/00* (2013.01); *A61K 38/04* (2013.01); *A61K 38/08* (2013.01); *A61K 38/09* (2013.01); *C07K 1/02* (2013.01); *C07K 1/026* (2013.01); *C07K 1/06* (2013.01); *C07K 1/10* (2013.01); *C07K 5/08* (2013.01); *C07K 7/00* (2013.01); *C07K 7/04* (2013.01); *C07K 7/23* (2013.01)

(58) Field of Classification Search
None
See application file for complete search history.

(56) References Cited

U.S. PATENT DOCUMENTS

| 3,773,919 | A | 11/1973 | Boswell |
| 5,506,207 | A | 4/1996 | Rivier et al. |
| 5,516,887 | A | 5/1996 | Deghenghi |
| 5,595,760 | A | 1/1997 | Cherif-Cheikh |
| 5,821,230 | A | 10/1998 | Jiang et al. |
| 5,860,957 | A | 1/1999 | Jacobsen et al. |
| 5,863,549 | A | 1/1999 | Taratino |
| 5,925,730 | A | 7/1999 | Semple et al. |
| 6,214,798 | B1 | 4/2001 | Semple et al. |
| 6,503,534 | B1 | 1/2003 | Pellet et al. |
| 2004/0038903 | A1 | 2/2004 | Luck et al. |
| 2004/0138610 | A1 | 7/2004 | Cormier et al. |
| 2005/0245455 | A1 | 11/2005 | Luck et al. |
| 2006/0135405 | A1 | 6/2006 | Rischer et al. |
| 2008/0032935 | A1 | 2/2008 | Engel et al. |
| 2009/0018085 | A1 | 1/2009 | Luck et al. |
| 2009/0203622 | A1 | 8/2009 | Persson |
| 2009/0209939 | A1 | 8/2009 | Verespej et al. |
| 2010/0286603 | A1 | 11/2010 | Winderstrom |
| 2010/0305042 | A1 | 12/2010 | Olesen et al. |
| 2011/0039787 | A1 | 2/2011 | Petri et al. |
| 2011/0053846 | A1 | 3/2011 | Luck et al. |
| 2012/0172302 | A1 | 7/2012 | Petri et al. |
| 2013/0018223 | A1 | 1/2013 | Joseph |
| 2013/0029910 | A1 | 1/2013 | van der Meulen et al. |
| 2013/0281661 | A1 | 10/2013 | Rasmusse et al. |
| 2013/0281662 | A1 | 10/2013 | Kalita et al. |
| 2013/0295166 | A1 | 11/2013 | Grenier et al. |

FOREIGN PATENT DOCUMENTS

| CN | 1411803 A | 4/2003 | |
| EP | 0 002 749 B1 | 10/1983 | |
| EP | 0 556 034 A1 | 8/1993 | |
| EP | 1 003 774 B1 | 5/2000 | |
| EP | 1630169 | 8/2007 | |
| EP | 1 967 202 A1 | 9/2008 | |
| WO | WO 97/34923 | 9/1997 | |
| WO | WO 98/46634 | 10/1998 | |
| WO | WO 99/26964 | * 6/1999 | ............... C07K 7/23 |
| WO | WO 99/26964 A1 | 6/1999 | |
| WO | WO 03/006049 A1 | 10/2003 | |
| WO | WO 2004/080413 A2 | 9/2004 | |
| WO | WO 2007/130809 A2 | 11/2007 | |
| WO | WO 2008/135989 A1 | 11/2008 | |
| WO | WO 2009/101533 A1 | 8/2009 | |
| WO | WO 2010/121835 | * 10/2010 | ............... C07K 7/23 |
| WO | WO 2011/004260 A2 | 1/2011 | |

OTHER PUBLICATIONS

Samant et al., J. Med. Chem. (2006) 49(12), 3536-3543.*
Bray, Nature Reviews (2003) 2, 587-593.*
Albertsen, et al. "Cardiovascular Morbidity Associated with Gonadotropin Releasing Hormone Agonist and an Antagonist," European Urology (2013), https://dx.doi.org/10.16/j.eururo.2013.10,032.
Andersson et al., "Large-Scale Synthesis of Peptides," Biopolymers (Peptide Science), pp. 227-250, 2000.
Austria_Codex Fachinformation 2006/2007.
Boccon-Gibod et al: "Optimizing Hormone Therapy in Advanced Disease" European Urology Supllements, vol. 4, No. 8, Nov. 1, 2005, pp. 21-29, XP005112815 ISSN: 1569-9056.
Boyle et al: "Treatment of hormone sensitive prostate cancer" European Journal of Cancer. Supplement, Pergamon, Oxford, GB, vol. 3, No. 3, Oct. 1, 2005, pp. 331-338, XP005130027 ISSN: 1359-6349.

Council of Europe, Strasbourg, "European Pharmacopoeia 6263" European Directorate for the Quality of Medicines & Healthcare (2007).
Debruyne Franse M J: "Gonadotropin-releasing hormone antagonist in the management of prostate cancer," Reviews in Urology 2004, vol. 6 Suppl 7, 2004, pp. S25-S32, XP002527257 ISSN: 1523-6161.
Degarelix Study Group Tammela et al: "904 Degarelix—a phase 11 multicenter, randomized dose-escalating study testing a novel gnrh receptor blocker in prostate cancer patients" European Urology Supplements, vol. 4, No. 3, Mar. 1, 2005, p. 228, XP005007365 ISSN: 1569-9056.
Doehn Christian et al: "Drug evaluation: Degarelix—a potential new therapy for prostate cancer." Drugs: The Investigational Drugs Journal Aug. 2006, vol. 9, No. 8, Aug. 2006, pp. 565-572, XP009105353 ISSN: 1369-7056.
European Patent Office Communication pursuant to Article 94(3) EPC dated Apr. 10, 2014, in corresponding Application No. 11 776 746.9 (5 pages).
Frampton et al, "Degarelix", ADIS International, Drugs, 69 (14): 1967-1976 (2009).
Garnick M et al: "217 Increase in the electrocardiographic QTC interval in men with prostate cancer undergoing androgen deprivation therapy: Results of three randomized controlled clinical studies", European Urology Supplements, vol. 3, No. 2, Feb. 1, 2004, p. 57, XP027186629, ISSN: 1569-9056.
Gittelman et al: "MP-08.21: A multicentre, randomised one year dose-finding study of degarelix, a gonadotrophin-releasing hormone (GnRH) receptor blocker in prostate cancer patients" Urology, Belle Mead, NJ, US vol. 70 No. 3, Sep. 1, 2007 pp. 83-84, XP022248654 ISSN:0090-4295.
Gonzalez-Barcena D et al: "Luteinzing hormone-releasing hormone antagonist centrorelix as primary single therapy in patients with advanced prostatic cancer and paraplegia due to metastatic invasion of spinal cord." Urology Feb. 1995, vol. 45, No. 2, Feb. 1995, pp. 275-281, XP02527258 ISSN: 0090-4295.
Huirne J A et al: "Gonadotropin-releasing-hormone-receptor antagonists" Lancet the, Lancet Limited. London, GB, vol. 358, No. 9295, Nov. 24, 2001, pp. 1793-1803, XP04805574 ISSN: 0140-6736.
Isidro-Llobet et al., "Amino Acid-Protecting Groups," Chem. Rev, pp. 2455-2504, 2009.
Iversen et al: "MP-08.18" Urology, Belle Mead, NJ, US, vol. 68, Nov. 1, 2006, p. 102, XP05709326 ISSN 0090-4295.
Keating Nancy L et al: "Diabetes and cardiovascular disease during androgen deprivation therapy for prostate cancer." Journal of Clinical Oncology: Official Journal of the American Society of Clinical Oncology Sep. 20, 2006, vol. 24, No. 27, Sep. 20, 2006, pp. 4448-4456, XP002687918, ISSN: 1527-7755.
Mongiat-Artus P et al: "Role of Luteinising Hormone Releasing Hormone (LHRH) Agonists and Hormonal Treatment in the Management of Prostate Cancer" European Urology Supplements, vol. 4, No. 5, Jul. 1, 2005, pp. 4-13, XP004926296 ISSN: 1569-9056.
Montalbetti et al., "Amide bond formation and peptide coupling," Science Direct (Tetrahedron 2005), pp. 10827-10852.
National Cholesterol Education Program (NCEP) Guidelines for Interpretation of Lipid Values, XP-02729834 (2001; Updated 2004).
NCEP ATP III Classification of Total Cholesterol, LDL-C, and HDL-C, XP-02729835 (2010).
Office Action (final) dated Jan. 9, 2014, U.S. Appl. No. 12/829,467.
Office Action (final) dated Mar. 5, 2014, U.S. Appl. No. 12/155,897.
Office Action (final) dated Mar. 6, 2014, U.S. Appl. No. 12/901,270.
Office Action (Final) mailed May 20, 2014, in co-pending U.S. Appl. No. 13/458,330.
Office Action mailed Aug. 27, 2014 in U.S. Appl. No. 13/881,744.
Office Action mailed Dec. 3, 2013, in copending U.S. Appl. No. 12/368,713.
Office Action mailed Oct. 2, 2014, in copending U.S. Appl. No. 12/829,467.
Samant et al., "Novel analogues of degarelix incorporating hydroxy-, methoxy- and pegylated-urea moieties at postions 3, 5, 6 and the N-terminus," J. Med Chem. 49(12), pp. 3536-3543, 2006.
Tsai Henry K et al: Androgen deprivation therapy for localized prostate cancer and the risk of cardiovascular mortality, Journal of the National Cancer Institute Oct. 17, 2007 LNKD-PUBMED:17925537, vol. 99, No. 20, Oct. 17, 2007, pp. 1516-1524, XP002687919, ISSN: 1460-2105.
van Kerrebroeck et al., "Desmopressin in the Treatment of Nocturia: A Double-Bind, Placebo-Controlled Study", European Urology, 52, (Jan. 16, 2007).
Van Poppel H et al: "23 Long-Term Evaluation of Degarelix, a Gonadotrophin-Releasing Hormone (GNRH) Receptor Blocker, Investigated in a Multicentre Randomised Study in Prostate Cancer (CAP) Patients" European Urology Supplements, vol. 6, No. 2, Mar. 1, 2007, p. 28, XP022686644 ISSN: 1569-9056 [retrieved on Mar. 1, 2007].
"Alkaline Phosphatase," GP Notebook (Sep. 12, 2011), http://gpnotebook.co.uk/simplepage.cfm?ID=-1932525548.
Agerso, et al., "The dosing solution influence on the pharmacokinetic of degarelix, a new GnRH antagonist, after s.c. administration to beagle dogs," European Journal of Pharmaceutical Sciences, vol. 20, pp. 335-340, 2003.
Behn, et al., "The obesity epidemic and its cardiovascular consequences," (2006) Curr. Opin. Cardiol. vol. 21, pp. 353-360.
Berges, et al., "Effect of a new leuprorelin formulation on testosterone levels in patients with advanced prostate cancer," (2006), Cur. Med. Res. Opin., vol. 22, No. 4, pp. 649-655.
Boccon-Gibod, et al., "Cyproterone Acetate Lead-In Prevents Initial Rise of Serum Testosterone Induced by Luteinizing Hormone-Releasing Hormone Analogs in the Treatment of Mestastatic Carcinoma of the Prostate," (1986) Euro. Urol.,vol. 12, pp. 400-402.
'Bone Specific Alkaline Phosphatase,' The University of Iowa (UIHC), Department of Pathology, Laboratory Services Handbook (Sep. 11, 2011), http://www.healthcare.uiowa.edu/path_handbook/handbook/test2238.html.
Broqua et al., "Effects of the New GNRH Antagonist FE200486 one the Growth of the Androgen-Dependent Prostate Tumor Dunning R-3327H, 6th International Symposium on GnRH Analogues in Cancer and Human Reproduction," Geneva, Switzerland, Feb. 8, 2001.
Broqua, et al., "Pharmacological Profile of a New, Potent, and Long-Acting Gonadotropin-Releasing Hormone Antagonist: Degarelix, The Journal of Pharmacology and Experimental Therapeutics," vol. 301, pp. 95-102, 2002.
Cetrotide TM package insert (Aug. 11, 2000).
Chernecky, and Berger, "Laboratory Tests and Diagnostic Procedures," (2008) Fifth Edition, WB Saunders & Company, Philadelphia. ISBN-978-1-14160-3704-0.
Crawford et al., "A Phase III Extension Trial With a 1-Arm Crossover From Leuprolide to Degarelix: Comparison of Gonadotropin-Releasing Hormone Agonist and Antagonist Effect of Prostate Cancer," 186 The Journal of Urology 889-897 (2011).
de la Rosette et al., "Efficacy and safety of androgen deprivation therapy after switching from monthly leuprolide to monthly degarelix in patients with prostate cancer," 65(5) International Journal of Clinical Practice 559-66 (2011).
de Pinieux, et al., "Clinical and Experimental Progression of a New Model of Human Prostate Cancer and Therapeutic Approach," American Journal of Pathology, vol. 159, No. 2, Aug. 2001, 753-764.
Debruyne, et al., "Abarelix for injectable suspension: first-in-class gonadotropin-releasing hormone antagonist for prostate cancer," (2006) Future Oncol., vol. 2, pp. 677-696.
Demers et al., "Biochemical Markers and Skeletal Metastases," Cancer, vol. 88, pp. 2919-2926, Mar. 2, 2000.
Denis, et al., "Overview of Phase III Trials on Combined Androgen Treatment in Patients with Metastatic Prostate Cancer," (1993) Cancer, vol. 72, pp. 3888-3895.
Eastman et al., "Serum Alkaline Phosphatase: Normal Values by Sex and Age," 23 (9) Clinical Chemistry 1769-1770 (1977).
Etzioni, et al., "Cancer Surveillance Series: Interpreting Trends in Prostate Cancer—Part III: Quantifying the Link Between Population Prostate-Specific Antigen Testing and Recent Declines in Prostate Cancer Mortality," (1999) J. Natl. Canc. Inst., vol. 91, pp. 1033-1039.
European Search Report & Opinion, dated Oct. 2, 2012, EP Application No. 12168495.5.
FDA Drug Information Page—Plenaxis (abarelix for injectable suspension); http://www.fda.gov/cder/drug/infopage/planaxis/default.htm. (Feb. 2004).

fda.gov, Label for Degarelix for injection (Dec. 24, 2008), available at www.accessdata.fda.gov/drugsatfda_docs/label/2008/022201lbl.pdf, last visited Jun. 4, 2013.
Ferlay, et al., "Estimates of the cancer incidence and mortality in Europe in 2006," Annals of Oncology, vol. 18, pp. 581-592 (2007).
Fleming, et al., "Post-therapy changes in PSA as an outcome measure in prostate cancer clinical Trials," (2006) Nature Clinical Practice Oncolology, vol. 3, No. 12, pp. 658-667.
Forbes, et al., "FDA's Adverse Drug Reaction Drug Dictionary and Its Role in Post-Marketing Surveillance," (1986) Drug Inf. J., vol. 20, pp. 135-145.
Gerlinger, et al., "Recommendation for Confidence interval and sample size calculations for the Pearl Index," (2003) The European Journal of Contraception and Reproductive Health Care, vol. 8, pp. 87-92.
Gillum, T., "The Merck Regulatory Dictionary: A Pragmatically Develop Drug Effects Vocabulary," (1989) Drug Info. J., vol. 23, pp. 217-220.
Gittelman et al., "A 1-Year, Open Label, Randomized Phase II Doe Finding Study of Degarelix for the Treatment of Prostate Cancer in North America," The Journal of Urology, vol. 80, pp. 1986-1992, Nov. 2008.
Granfors, et al., "Combined Orchiectomy and External Radiotherapy Versus Radiotherapy Alone for Nonmetastatic Prostate Cancer With or Without Pelvic Lymph Node Involvement: A Prospective Randomized Study," J. Urol., (1998), 159:2030-34.
Hackman, et al., "Emerging Risk Factors for Atheroslerotic Vascular Disease," (2003), JAMA, vol. 290, pp. 932-940.
Hegele et al., "Biochemical Markers of Bone Turnover in Patients with Localized and Metastasized Prostate Cancer," Journal Compilation, vol. 99, pp. 330-334, Sep. 7, 2006.
Hellerstedt, et al., "The Current State of Hormonal Therapy for Prostate Cancer," CA A Cancer Journal for Clinicians, vol. 52, pp. 154-179. (2002).
International Search Report issued on Apr. 19, 2012, in Application No. PCT/EP2012/050695.
International Search Report issued on Sep. 12, 2002, in Application No. PCT/GB02/03116.
Iversen et al., "Improved outcomes with degarelix monotherapy compared with luteinizing hormone-releasing hormone (LHRH) agonists plus antiandrogen in the treatment of men with advanced prostate cancer", 29th Congress of the Scandinavian Association of Urologiest, May 22, 2013, 2 pages.
Jiang et al., "Betidamino Acid-Scan of the GNRH Antagonist Acyline," Journal of Medicinal Chemistry, American Chemical Socitey, Washington, US, vol. 40, 1997, pp. 3739-3748.
Jiang, et al.,"GnRH Antagonists: A New Generation of Long Acting Analogues Incorporating p-Ureido-phenylalanies at Positions 5 and 6," (2001) J. Med. Chem., vol. 44, pp. 453-467.
Kirk et al., "Immediate Versus deferred treatment for advanced prostatic cancer; initial results of the Medical Research Counsel trial.," British Journal of Urology, (1997) vol. 79, pp. 235-246.
Lehmann, "Testing Statistical Hypotheses," (1986) Second Edition, John Wiley & Sons, New York, ISBN 0-471-84083-1.
Lilja, et al., "Prostate-specific antigen and prostate cancer: prediction, detection and monitoring," (2008) Nature Reviews/Cancer, vol. 8, pp. 268-278.
Lukka, et al., "Maximal androgen blockade for the treatment of metastatic prostate cancer—a systematic review," Current Oncology, vol. 13, No. 3, pp. 81-93. (2006).
Lyseng-Williamson, Katherine A., "Degarelix: a guide to its use in advanced prostate cancer," 28(5) Drugs Ther. Perspect. 6-10 (2012).
Malkin, "Are techniques used for intramuscular injection based on research evidence?" nursingtimes.net, Nursing Times; 104; 50/51, 48-51 Dec. 16, 2008.
McNeil, et al., "On the Elicitation of Preferences for Alternative Therapies," (1982) N. Engl. J. Med., vol. 306, No. 21, pp. 1259-1262.
MedDRA website, http://www.meddramsso.com. (2009).
Messing, et al., "Immediate Hormonal Therapy Compared with Observation after Radical Prostatectomy and Pelvic Lyphadenectomy in Men with Node-Positive Prostate Cancer," (1999), N. Eng. J. Med., vol. 341, pp. 1781-1788.

Mongiat-Artus, et al., "Abarelix: the first gonadotrophin-releasing hormone antagonist for the treatment of prostate cancer," (2004), Expert Opin. Pharmacother, vol. 5, pp. 2171-2179.
Office Action (final) dated Oct. 8, 2013, U.S. Appl. No. 13/381,762.
Office Action dated Jul. 25, 2013, U.S. Appl. No. 12/829,467.
Office Action dated Jul. 26, 2013, U.S. Appl. No. 12/901,270.
Office Action dated Jun. 11, 2013, U.S. Appl. No. 13/381,762.
Office Action dated Jun. 6, 2013, U.S. Appl. No. 12/774,113.
Office Action dated Sep. 11, 2013, in U.S. Appl. No. 12/771,199.
Office Action dated Sep. 3, 2013, in U.S. Appl. No. 13/458,330.
Office Action mailed Apr. 2, 2012, in copending U.S. Appl. No. 12/368,935.
Office Action mailed Jan. 31, 2013, in copending U.S. Appl. No. 12/901,270.
Office Action mailed Mar. 1, 2011, in copending U.S. Appl. No. 12/368,713.
Office Action mailed Mar. 8, 2011, in copending U.S. Appl. No. 12/155,897.
Office Action mailed Oct. 12, 2011, in U.S. Appl. No. 12/155,897.
Office Action mailed Oct. 22, 2009, in co-pending U.S. Appl. No. 12/155,897.
People's Republic of China First Office Action dated Feb. 25, 2013 in corresponding Application No. 201080019696.2, 2 pages.
Persad, "Leuprorelin Acetate in Prostate Cancer: A European Update," (2002) Int. J. Clin. Pract., vol. 56, No. 5, pp. 389-396.
Romero-Corral, et al., "Association of bodyweight with total mortality and with cardiovascular events in coronary artery disease: a systematic review of cohort studies," (2006) Lancet, 368:666-678.
Saltzman, A., "Adverse Reaction Terminology Standardization: A Report on Schering-Plough's Use of the WHO Dictionary and the Formation of the WHO Adverse Reaction Terminology Users Group (WUG) Consortium," (1985) Drug Info. J., vol. 19, pp. 35-41.
Smith et al., "Cardiovascular Safety of Degarelix: Results From a 12-Month, Comparative, Randomized, Open Label, Parallel Group Phase III Trial in Patients With Prostate Cancer," 184 The Journal of Urology 2313-2319 (2010).
Smith, M.R. et al., "Gonadotropin-Releasing Hormone Blockers and Cardiovascular Disease Risk: Analysis of Prospective Clinical Trials of Degarelix," 186 The Journal of Urology 1835-1842 (2011).
Sorbera et al., "Degarelix Acetate", GnRH Antagonist Prostate Cancer Therapy; Drugs of the Future 2006, vol. 31, No. 9, pp. 755-766.
Spilker, Bert, "Guide to Clinical Trials," (1991) Raven Press, Ltd., New York, ISBN 0-88167-767-1.
Spilker, Bert, "Quality of Life and Pharmacoeconomics in Clinical Trials," (1996) Lippincott—Raven Publishers, New York, ISBN 0-7817-0332-8.
Steinberg, et al., "Degarelix: A Gonadotropin-Releasing Hormone Antagonist for the Management of Prostate Cancer," Clinical Therapeutics, vol. 31, pp. 2312-2331, 2009.
Stephens, M.D.B., "The Detection of New Adverse Drug Reactions," (1988) Stockton Press, New York, ISBN 0-333-45417-0.
Teal, et al., "Adverse Drug Experience Management: A Brief Review of the McNeil Pharmaceutical System," (1985) Drug Info. J., vol. 19, pp. 17-25.
The K-Zone, Biophysical data tables: standard man, Jul. 2004; printed Mar. 14, 2009 from www.kevinboone.com/biodat_stdman.html; 1 page.
Thompson, et al., "Sudden Death to Disease Flare With Luteinizing Hormone-Releasing Hormone Agonist Therapy for Carcinoma of the Prostate," J. Urol., (1990) vol. 144, pp. 1479-1480.
Turner, et al., "The Processing of Adverse Reaction Reports at FDA," (1986) Drug. Inf. J., vol. 20, pp. 147-150.
Van Poppel et al., "A One-Year, Multicentre, Randomised Study of Degarelix a Gonadatrophin-Releasing Hormone (GNRH) Receptor Blocker, in Prostate Cancer Patients," Eur Urol Supppl 2005:5(2):251.
Van Poppel, "Evaluation of degarelix in the management of prostate cancer," Cancer Management and Research, vol. 2, pp. 39-52, 2010.
Wilson, et al., "Leuprolide acetate: a drug of diverse clinical applications," Expert Opin. Investig. Drugs, (2007) vol. 16, pp. 1851-1863.
Wilson, et al., "Prediction of Coronary Heart Disease Using Risk Factor Categories," (1998) Circulation, 97:1837-47.

Yannucci, et al., "The Effect of Androgen Deprivation Therapy on Fasting Serum Lipid and Glucose Parameters," (2006) J. Urol., vol. 176, pp. 520-525.

* cited by examiner

*Primary Examiner* — Marcela M Cordero Garcia
*Assistant Examiner* — Catherine Mader
(74) *Attorney, Agent, or Firm* — Finnegan, Henderson, Farabow, Garrett & Dunner, LLP

(57) ABSTRACT

The present invention relates to a liquid (or solution)-phase manufacturing process for preparing the decapeptide Degareiix, its amino-protected precursor, and other useful intermediates. The invention further relates to polypeptides useful in the solution-phase manufacturing process and to the purification of Degareiix itself. The manufacturing process comprises the step of cleaving the ε-amino protecting group Pε from a Degareiix precursor according to formula {$P_4$}(Pε)Ac-$AA_1$-$AA_{10}$-$NH_2$ in an organic solvent comprising the precursor and a cleaving agent dissolved therein: wherein $P_4$ is a hydroxyl-protecting group or hydrogen, preferably hydrogen.

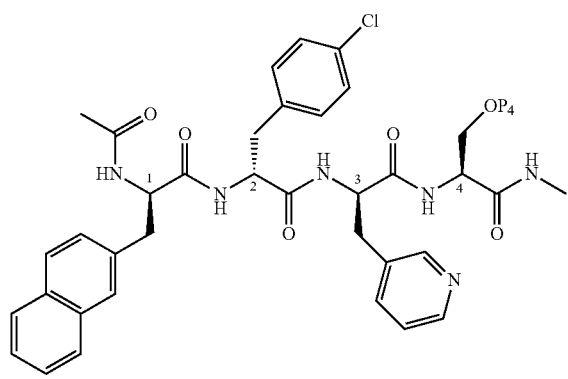

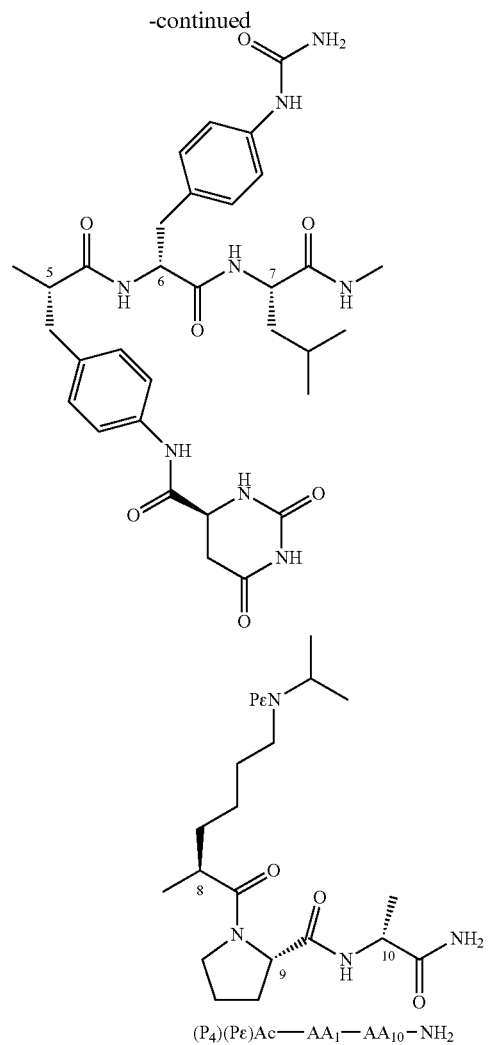

26 Claims, 8 Drawing Sheets

Figure 1:
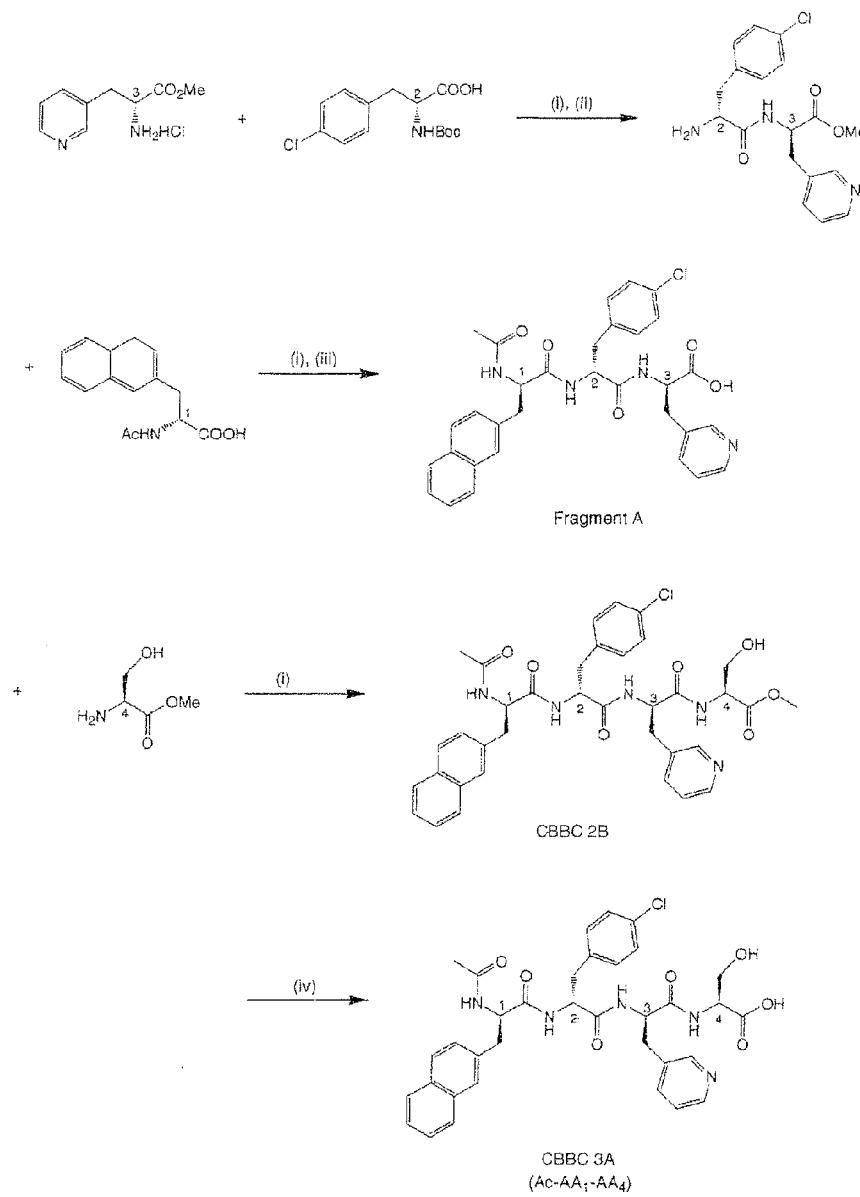

Conditions: (i) EDC.HCl, HOBt; (ii) HCl/MeOH; (iii) LiOH, DMF; (iv) aq. LiOH, THF

PROCESS FOR THE MANUFACTURE OF DEGARELIX AND ITS INTERMEDIATES

This is a national stage entry application of International Patent Application No. PCT/EP2011/068733, filed Oct. 26, 2011, which claims the benefit of priority of European Patent Application No. 10189011.9, filed Oct. 27, 2010, both of which are incorporated herein by reference in their entireties.

TECHNICAL FIELD

The present invention relates to a liquid (or solution)-phase manufacturing process for preparing the decapeptide Degarelix, its amino-protected precursor, and other useful intermediates. The invention further relates to polypeptides useful in the solution-phase manufacturing process and to the purification of Degarelix itself.

BACKGROUND OF THE INVENTION

Prostate cancer is a leading cause of morbidity and mortality for men in the industrialised world. Degarelix, also known as FE200486, is a third generation gonadotropin releasing hormone (GnRH) receptor antagonist (a GnRH blacker) that has been developed and recently approved for prostate cancer patients in need of androgen ablation therapy (Doehn et al., Drugs 2006, vol. 9, No. 8, pp. 565-571; WO 09846634). Degarelix acts by immediate and competitive blockade of GnRH receptors in the pituitary and, like other GnRH antagonists, does not cause an initial stimulation of luteinizing hormone production via the hypothalamic-pituitary-gonadal axis, and therefore does not cause testosterone surge or clinical flare (Van Poppel, Cancer Management and Research, 2010:2 39-52; Van Poppel et al., Urology, 2008, 71(6), 1001-1006; James, E. F. et al., Drugs, 2009, 69(14), 1967-1976).

Degarelix is a synthetic linear decapeptide containing seven unnatural amino acids, five of which are D-amino acids. It has ten chiral centers in the back bone of the decapeptide. The amino acid residue at position 5 in the sequence has an additional chiral center in the side-chain substitution giving eleven chiral centers in total. Its CAS registry number is 214766-78-6 (of free base) and it is commercially available under the Trademark Firmagon™. The drug substance is chemically designated as D-Alaninamide, N-acetyl-3-(2-naphthalenyl)-D-alanyl-4-chloro-D-phenylalanyl-3-(3-pyridinyl)-D-alanyl-L-seryl-4-[[[(4S)-hexahydro-2,6-diaxo-4-pyrimidinyl]carbonyl]amino]-L-phenylalanyl-4-[(aminocarbonyl)amino]-D-phenylalanyl-L-leucyl-N6-(1-methylethyl)-L-lysyl-L-prolyl- and is represented by the chemical structure below:

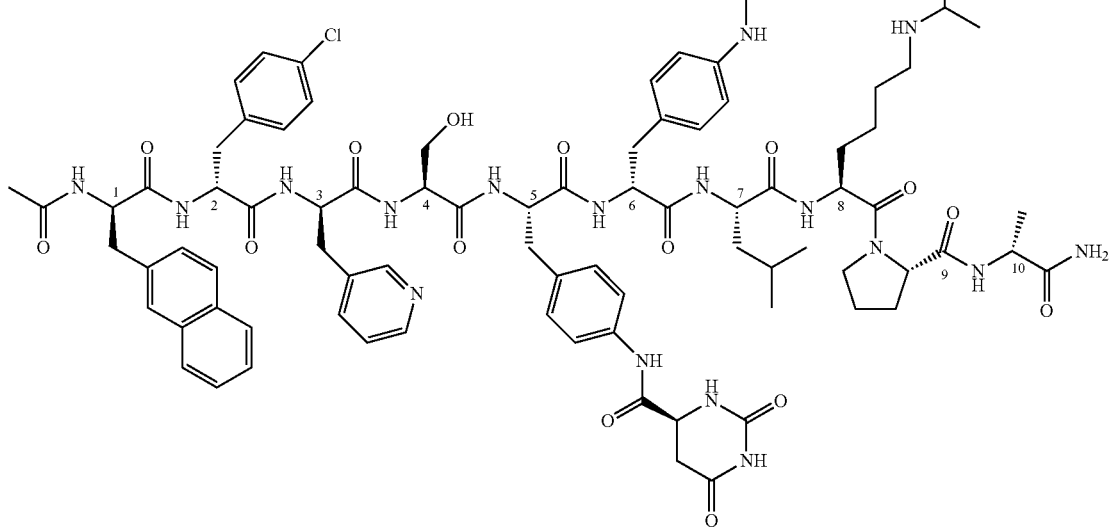

The structure of Degarelix can also be represented as:

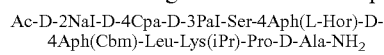

where Ac is acetyl, 2NaI is 2-naphthylalanine, 4 Cpa is 4-chlorophenylalanine, 3 PaI is 3-pyridylalanine, Ser is serine, 4Aph is 4-aminophenylalanine, Hor is hydroorotyl, Cbm is carbamoyl, Leu is leucine, Lys(iPr) is N6-isopropyllysine, Pro is proline and Ala is alanine.

For the purposes of describing this invention, each amino acid in Degarelix will be given the shorthand notation as follows:
$AA_1$ is D-2NaI, $AA_2$ is D-4 Cpa, $AA_3$ is D-3 PaI, $AA_4$ is Ser, $AA_5$ is 4Aph(L-Hor), $AA_6$ is D-Aph(Cbm), $AA_7$ is Leu, $AA_8$ is Lys(iPr), $AA_9$ is Pro and $AA_{10}$ is D-Ala.

Thus, as an example, Degarelix can be represented as Ac-$AA_1$-$AA_{10}$-$NH_2$, the tetrapeptide Ac-D-2NaI-D-4 Cpa-D-3 PaI-Ser can be represented as Ac-$AA_1$-$AA_4$ and the hexapeptide 4Aph(L-Hor)-D-4Aph(Cbm)-Leu-Lys(iPr)-Pro-D-Ala-$NH_2$ as $AA_5$-$AA_{10}$-$NH_2$.

Degarelix has previously been prepared using Boc-solid phase peptide synthesis (SPPS) methodology as reported in WO 98/46634 and Jiang et al., J. Med. Chem. 2001, 44, 453-467. Basically, Boc-protected D-Ala is first coupled to MBNA resin in dimethylformamide (DMF)/$CH_2Cl_2$ using diisopropylcarbodiimide (DIC) and 1-hydroxybenzotriazole (HOBt) as activating or coupling agents. Once D-Ala is coupled to the resin, synthesis proceeds by washing, deblocking and then coupling the next amino acid residue until the decapeptide has been completed. The side chain primary amino groups of 4Aph in the 5-position and of D-4Aph in the 6-position are protected by Fmoc when they are added and modified with L-Hor and Cbm respectively before the next amino acid in the chain is added. This requires the additional steps of first removing the side-chain protection with piperidine, reacting the newly freed amino group on the peptidoresin with tert-butyl isocyanate or L-hydroorotic acid, ensuring that the reaction is complete with a ninhydrin test and then washing the peptidoresin before adding the next amino acid residue (see also Sorbera et al., Drugs of the Future 2006, Vol. 31, No. 9, pp 755-766).

While Boc-SPPS methodology has afforded sufficient quantities of Degarelix until now, the growing demand for this polypeptide means that ever larger quantities are required. Boc-SPPS, which requires HF cleavage, is not suited to large scale industrial synthesis. Indeed, WO 98/46634 mentions that SPPS is only suitable for limited quantities of up to 1 kg while classical peptide solution synthesis, or liquid phase peptide synthesis (LPPS), is preferred for larger quantities of product. WO 98/46634 does not specify how such synthesis should be performed. Further, expense attributable the large excess of coupling reagents, additives, and amino acids required for the SPPS. While the existence of a liquid phase peptide synthesis of Degarelix has been reported [EMEA Report: Assessment Report for Firmagon™ (Degarelix): Doc. Ref. EMEA/CHMP/635761/2008], as of now no details of such a process have been publically disclosed.

WO 97/34923 and WO 99/26964 are international Application Publications which are concerned with liquid phase processes for the preparation of biologically active peptides. WO 99/26964 is particularly concerned with the liquid phase synthesis of decapeptides having activity as GnRH antagonists. WO 99/26964 lists a number of inherent limitations of the SPPS methodology for producing GnRH antagonists including the limited capacity of the resin, the large excess of reagents and amino acids required, as well as the need to protect all reactive side chains such as the hydroxy group in Ser, the aromatic amino groups in Aph and D-Aph, the ε-i-propylamino group in Lys(i-Pr).

International Application Publication No. WO 99/26964 describes a liquid phase process which involves first preparing the central peptide fragments of the 5 and 6 positions of a decapeptide with the side chains fully elaborated and then assembling the peptide through a "4-2-4", "3-3-4" or "3-4-3" fragment assembly pattern. For example, in the preparation of the GnRH antagonist Azaline B, a tetrapeptide is coupled with a hexapeptide to form the desired decapeptide. When the same fragment assembly pattern is attempted for Degarelix, racemisation of the Serine amino acid ($AA_4$) occurs resulting in about 20% impurity of L-Ser. This impurity carries over into the final decapeptide and is difficult to remove. Furthermore, when preparing the tetrapeptide $AA_1$-$AA_4$ by adding the Ser unit to the tripeptide $AA_1$-$AA_3$ following the procedure described in WO 99/26964, tetrabutylammonium ions from the hydrolysis of the benzyl ester group could not be removed completely during the subsequent operations and were carried through to the final product. It was further found that in the Degarelix synthesis, the L-hydroorotyl group rearranges to its hydantainacetyl analogue when L-dihydroorotic acid is coupled with 4 Amp to prepare $AA_5$. These and other problems with the solution-phase synthesis of Degarelix have now been overcome and a new solution-phase polypeptide synthesis of this decapeptide is disclosed herein for the first time.

SUMMARY OF THE INVENTION

The problems of SSPS methods for preparing Degarelix and the drawbacks of LLPS methods as described in WO 97/34923 and WO 99/26964 have now been overcome and are the subject of this invention.

In general, this invention relates to a liquid-phase synthesis of the decapeptide Degarelix.

In one aspect, the invention relates to a liquid-phase process for preparing Degarelix having the formula Ac-$AA_1$-$AA_{10}$-$NH_2$ or a pharmaceutically acceptable salt or solvate thereof, comprising the step of cleaving the ε-amino protecting group Pε from a Degarelix precursor according to formula ($P_4$)(Pε)Ac-$AA_1$-$AA_{10}$-$NH_2$ in an organic solvent comprising the precursor and a cleaving agent dissolved therein:

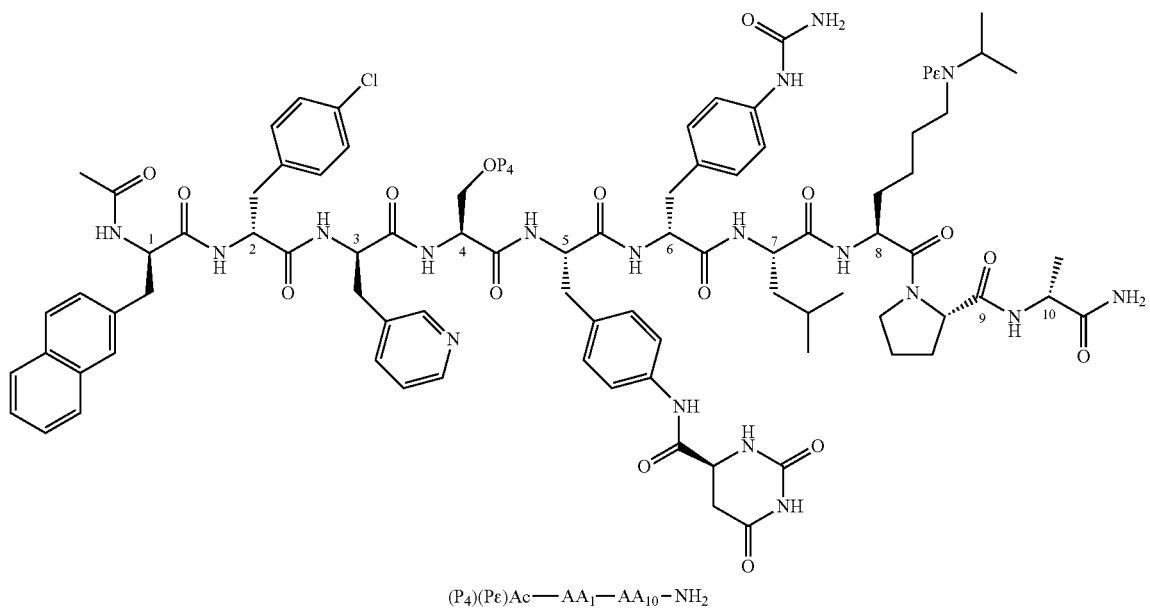

($P_4$)(Pε)Ac—$AA_1$—$AA_{10}$-$NH_2$

P$_4$ is a hydroxyl-protecting group or hydrogen, preferably, tBu, (ψPro) (i.e. pseudo-proline), or hydrogen. If P4 is a hydroxyl-protecting group, the process also comprises the step of cleaving the hydroxyl-protecting group P$_4$ from the Degarelix precursor. The protecting group P$_4$ is preferably selected in such a way that this cleavage step can be carried out simultaneously with the cleavage of the amino-protecting group Pε. This is for example the case if both P$_4$ and Pε are BOC.

In a second aspect, the invention also relates to a liquid-phase process for preparing a protected Degarelix precursor having the formula (P$_4$)(Pε)Ac-AA$_1$-AA$_{10}$-NH$_2$ or a pharmaceutically acceptable salt or solvate thereof, comprising the step of coupling (P$_4$)Ac-AA$_1$-AA$_4$ with (Pε)AA$_5$-AA$_{10}$NH$_2$ or coupling Ac-AA$_1$-AA$_3$ with (P$_4$)(Pε)AA$_4$-AA$_{10}$NH$_2$ in an organic solvent comprising the two peptides, a peptide coupling reagent and an organic amine base dissolved therein wherein Pε is an amino protecting group. The peptides are represented below:

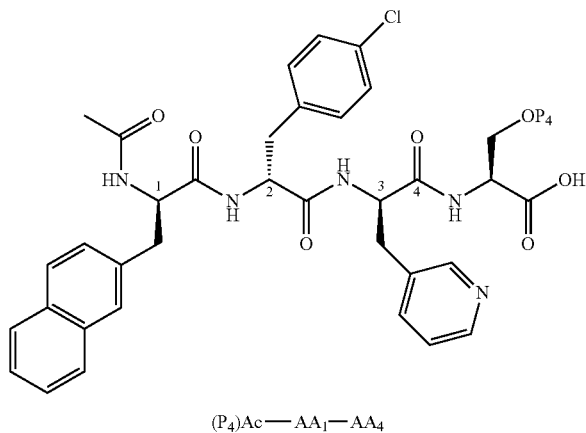

(P$_4$)Ac—AA$_1$—AA$_4$

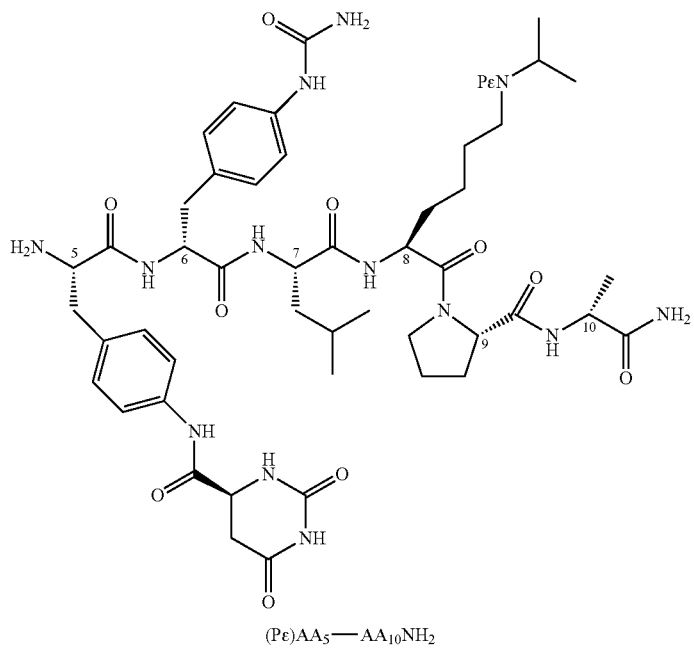

(Pε)AA$_5$—AA$_{10}$NH$_2$

-continued

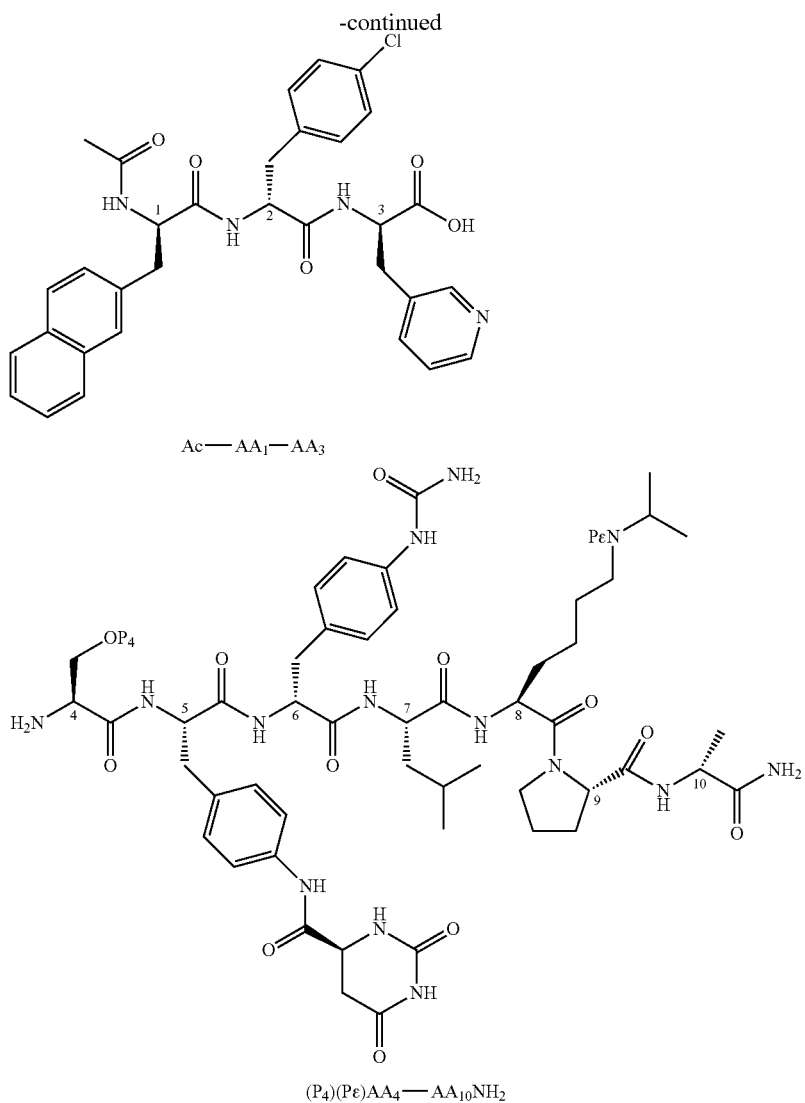

Ac—AA$_1$—AA$_3$ (P$_4$)(Pε)AA$_4$—AA$_{10}$NH$_2$

A third aspect concerns the liquid-phase process for preparing a Degarelix intermediate having the formula (P$_4$)Ac-AA$_1$-AA$_4$:

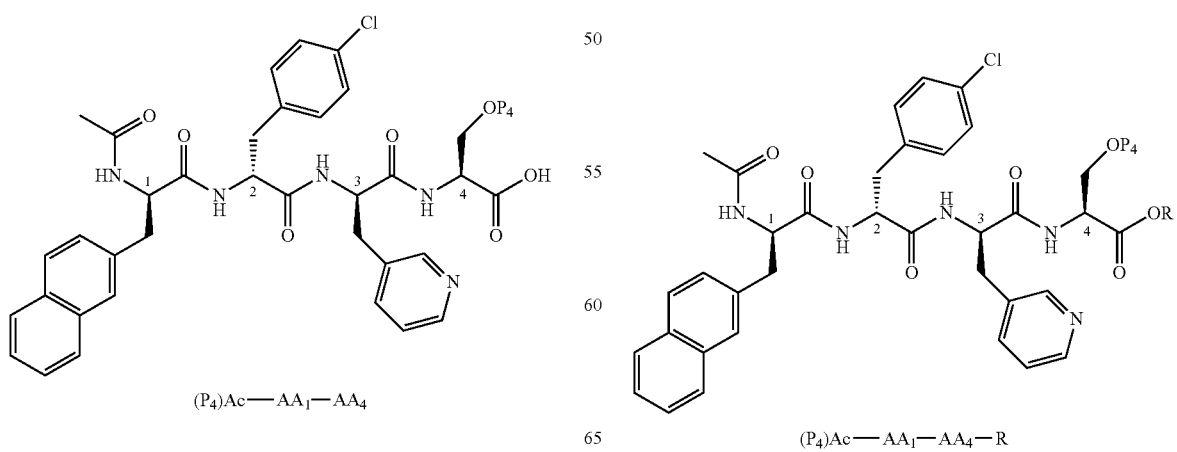

(P$_4$)Ac—AA$_1$—AA$_4$ or a pharmaceutically acceptable salt or solvate thereof, comprising the step of hydrolyzing a compound having the formula (P$_4$)Ac-AA$_1$-AA$_4$-R with an alkaline hydroxide, wherein R represents a carboxyl protecting group, preferably C$_1$-C$_4$ alkyl or benzyl:

(P$_4$)Ac—AA$_1$—AA$_4$—R

A fourth aspect concerns a process for preparing the compound $(P_4)Ac\text{-}AA_3\text{-}AA_4\text{-}R$ by coupling $Ac\text{-}AA_1\text{-}AA_3$ with $(P_4)AA_4\text{-}R$ or coupling $Ac\text{-}AA_1\text{-}AA_2$ with $(P_4)AA_3\text{-}AA_4\text{-}R$, the peptides being represented below

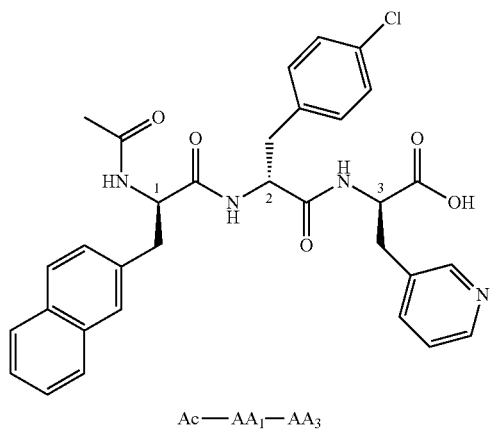

Ac—AA$_1$—AA$_3$

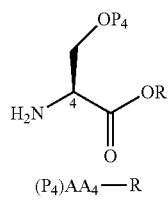

$(P_4)AA_4$—R

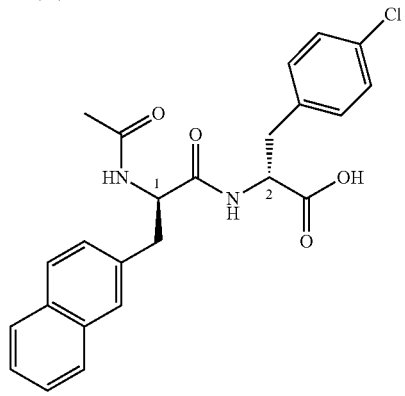

Ac—AA$_1$—AA$_2$

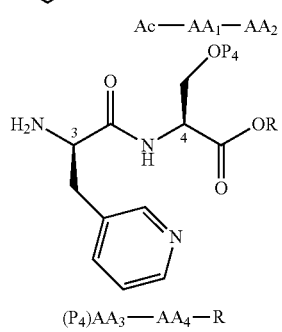

$(P_4)AA_3$—AA$_4$—R

In each of the formulae described above, $AA_1$ to $AA_{10}$, $P_4$ and $P_\epsilon$ have the same meanings as in formula II, and R represents a carboxyl protecting group, preferably $C_1\text{-}C_4$ alkyl or benzyl In a fifth aspect, the tetrapeptide $(P4)Ac\text{-}AA_1\text{-}AA_4$ is prepared not by liquid phase synthesis, but by solid phase synthesis. This invention thus also relates to a solid-phase process for preparing a Degarelix intermediate having the formula $(P4)Ac\text{-}AA_1\text{-}AA_4$:

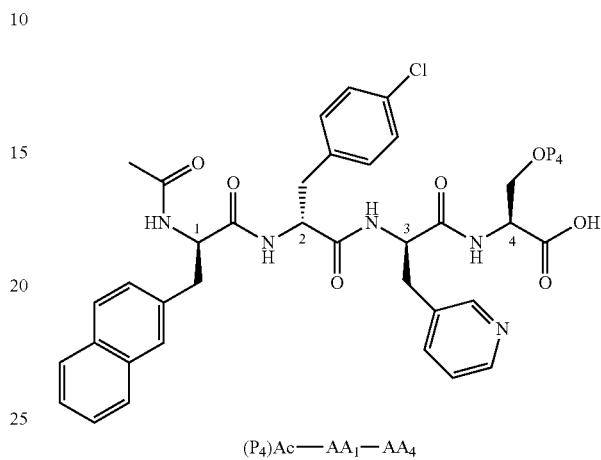

$(P_4)Ac$—AA$_1$—AA$_4$ or a pharmaceutically acceptable salt or solvate thereof, comprising the steps:

a) reacting (PN)AA2 with

to provide

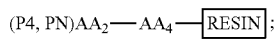

b) removal of PN from

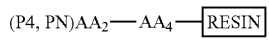

to provide

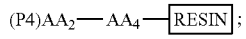

c) reacting (PN)AA1 with (P4)AA$_2$—AA$_4$—RESIN to provide (P4, PN)AA₁—AA₄—[RESIN];

d) if PN is not acetyl, removal of PN from (P4, PN)AA₁—AA₄—[RESIN]

to provide (P4)AA₁—AA₄—[RESIN]

and subsequently acetylating (P4)AA₁—AA₄—[RESIN]

to provide (P4)Ac—AA₁—AA₄—[RESIN];

and e) cleaving (P4)Ac—AA₁—AA₄—[RESIN]

to provide (P4)AC-AA₁-AA₄.

wherein P4 is H or a hydroxyl protecting group on AA4, and PN is an amino protecting group.

A sixth aspect of the invention concerns liquid-phase process for preparing the hexapeptide (Pε)AA₅-AA₁₀NH₂ comprising the coupling of (Pε)AA₆-AA₁₀NH₂ and (P$_X$)AA₅, wherein P$_X$ is an amino protecting group and AA₅ to AA₁₀ and Pε have the same meaning as above, to provide (P$_X$)(Pε)AA₅-AA₁₀NH₂, and cleaving Px with TFA to provide (Pε)AA₅-AA₁₀NH₂, the peptides being represented below:

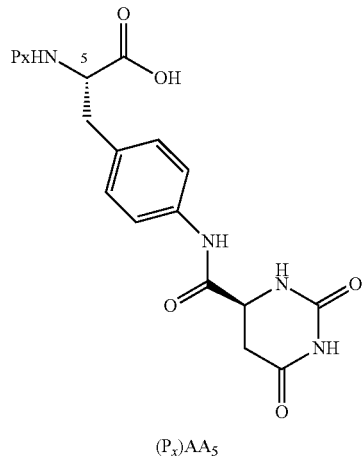

(P$_x$)AA₅

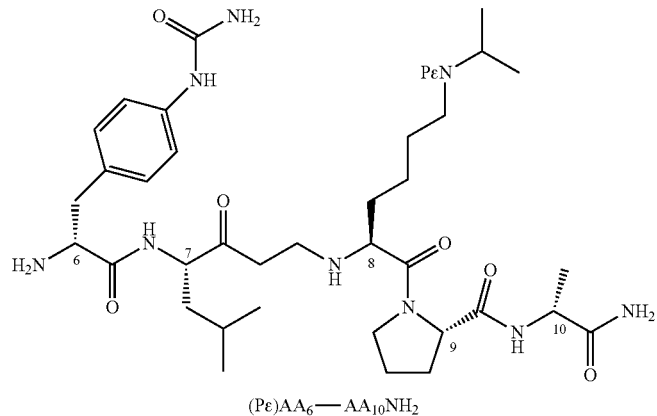

(Pε)AA₆—AA₁₀NH₂

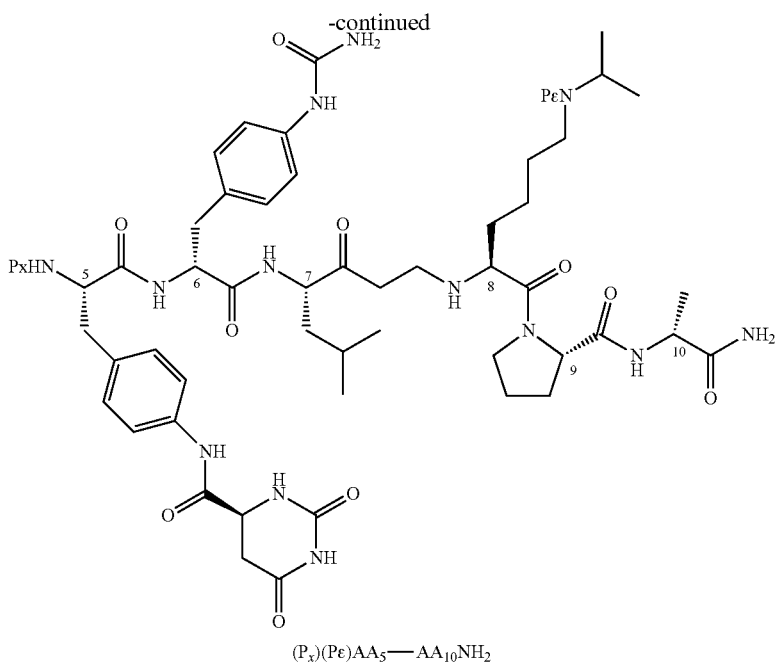

$(P_x)(P\epsilon)AA_5$—$AA_{10}NH_2$

A seventh aspect of the invention concerns a liquid-phase process for preparing the hexapeptide $(Px)(P\epsilon)AA_5$-$AA_{10}NH_2$ comprising the coupling of $(Px)AA_5$-$AA_7$ with $(P\epsilon)AA_8$-$AA_{10}NH_2$.

An eighth aspect of the invention concerns processes for purifying Degarelix, such as by preparative HPLC using PLRP—S and/or C8 and C18 columns.

It should be understood that in the process of preparing Degarelix according to this invention, any of the above process steps may be combined. For example, this invention also embodies a process in which $(P_4)Ac$-$AA_1$-$AA4$ is first prepared from $(P_4)Ac$-$AA_1$-$AA_4$-R according to the third aspect of the invention or according to the fifth aspect of the invention before being coupled with $(P\epsilon)AA_5$-$AA_{10}$-$NH_2$ to form the protected precursor $(P_4)(P\epsilon)Ac$-$AA_1$-$AA_{10}$-$NH_2$ according to the second aspect of the invention. The precursor $(P_4)$ $(P\epsilon)Ac$-$AA_1$-$AA_{10}$-$NH_2$ formed by such a process may then be deprotected according to the first aspect of the invention ultimately giving a single process for preparing Degarelix that incorporates the first, second and third or fifth aspects of the invention.

Naturally, any of the purification steps for Degarelix that are described herein may be incorporated into any process in which Degarelix is the final product.

FIGURES

FIG. 1. Liquid phase preparation of the tetrapeptide Ac-$AA_1$-$AA_4$

Figure 2:
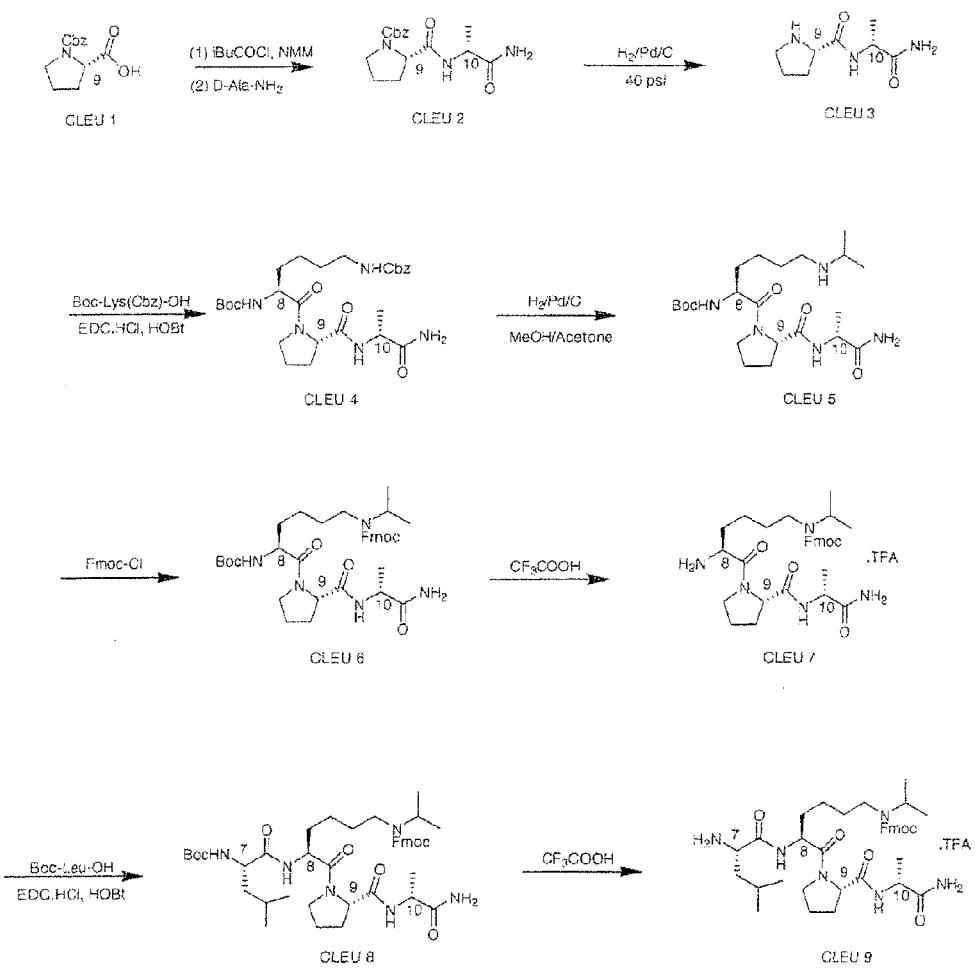
Figure 2:
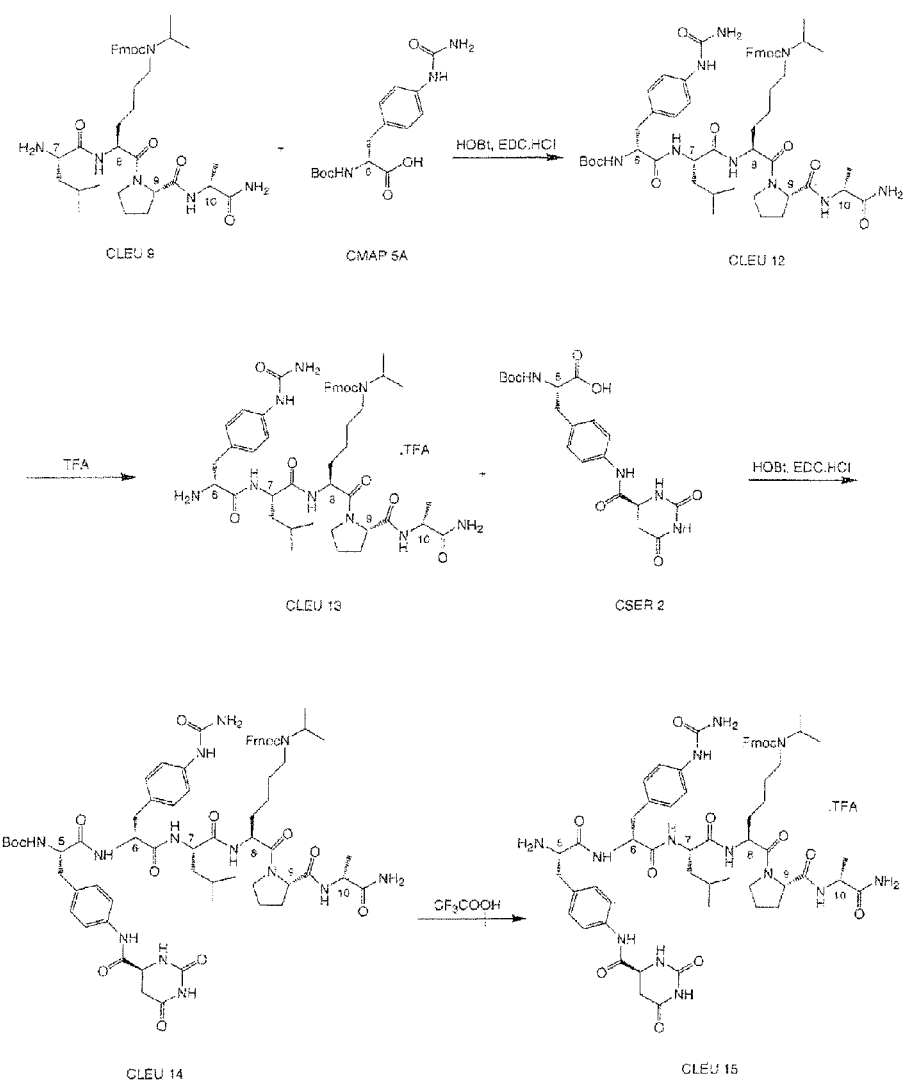

FIG. 2. Preparation of the $P\epsilon$ protected hexapeptide $AA_5$-$AA_{10}NH_2$ where $P\epsilon$ is Fmoc.

Figure 3:
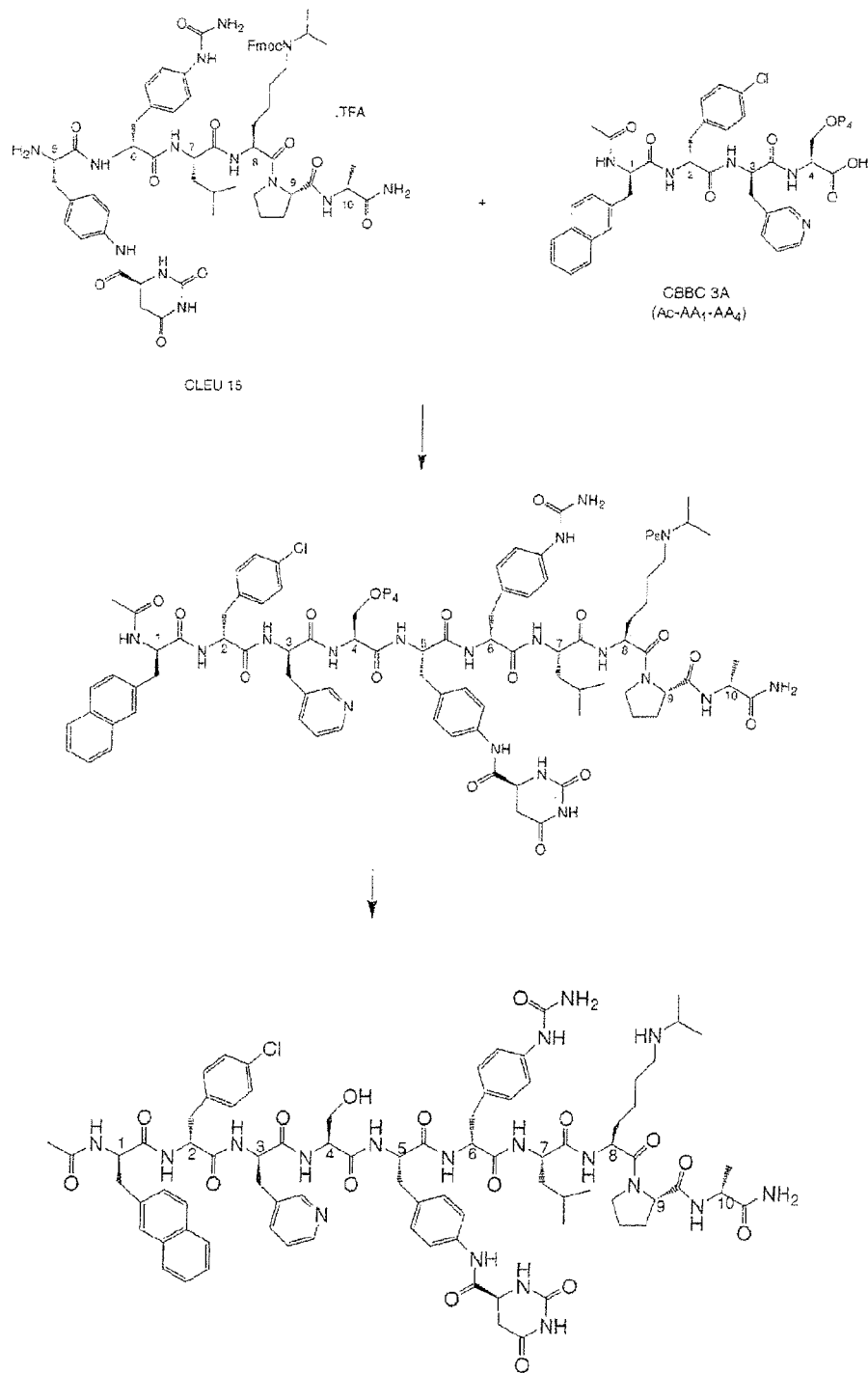

FIG. 3. Segment condensation and deprotection to yield Degarelix.

Figure 4:
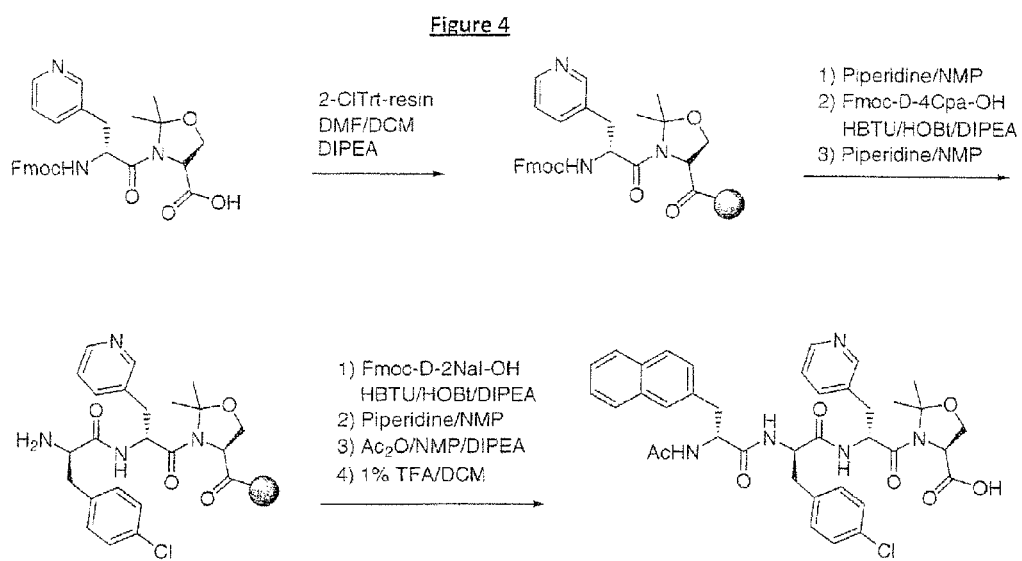

FIG. 4: Solid phase preparation of the tetrapeptide Ac-$AA_1$-$AA_4$ with a pseudoproline protecting group on AA4.

Figure 5:
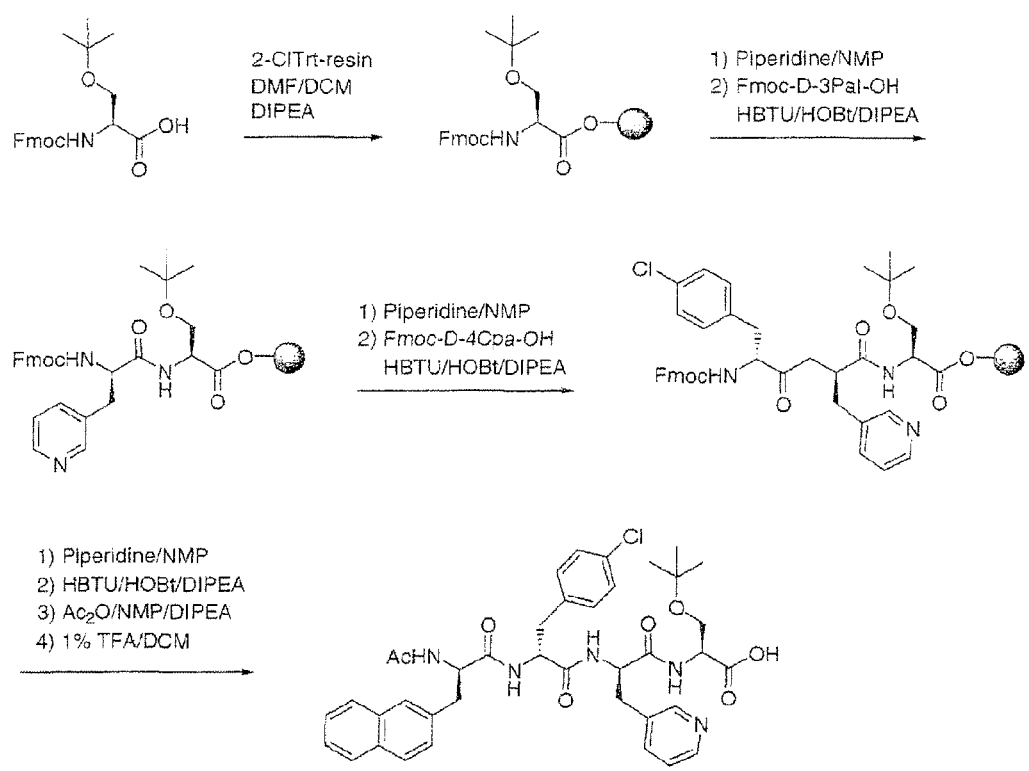

FIG. 5: Solid phase preparation of the tetrapeptide Ac-$AA_1$-$AA_4$ with a tBu protecting group on AA4.

Figure 6:
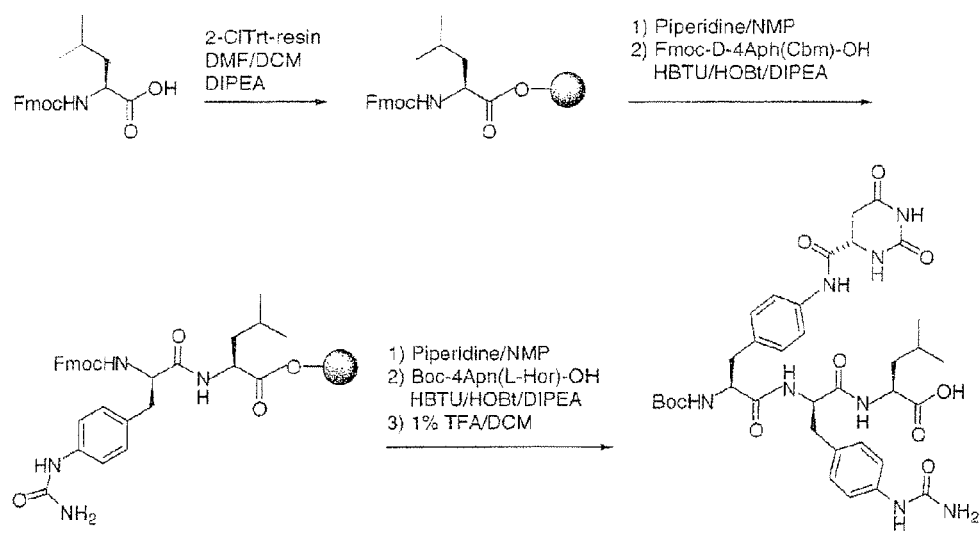

FIG. 6: Solid phase preparation of BOC-protected $AA_5$-$AA_7$

Figure 7:
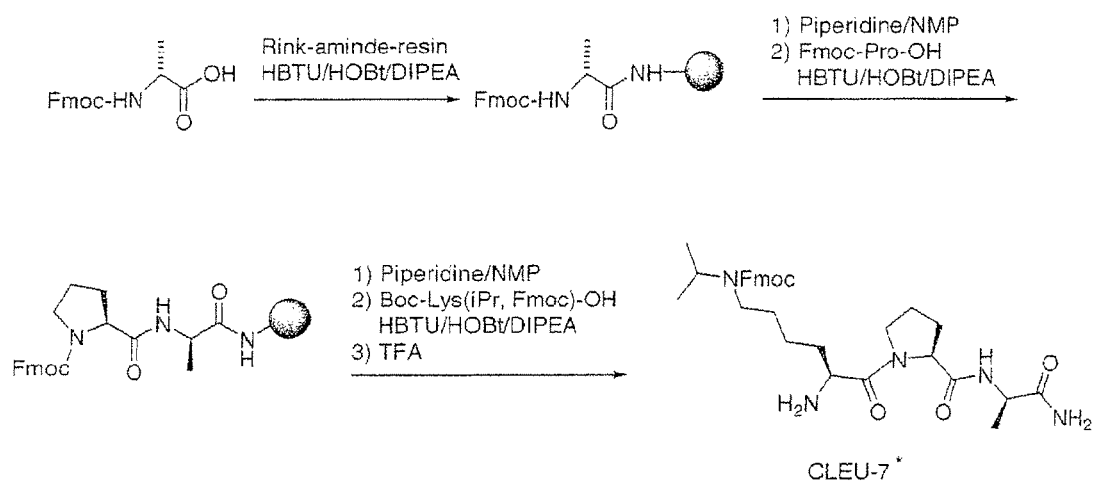

FIG. 7: Solid phase preparation of Fmoc-protected $AA_8$-$AA_{10}NH_2$.

DETAILED DESCRIPTION OF THE INVENTION

The present invention will now be described in more detail.
Deprotection of the Degarelix Precursor In a first aspect, the present invention relates to a liquid-phase process for preparing Degarelix having the formula Ac-$AA_1$-$AA_{10}$-$NH_2$ or a pharmaceutically acceptable salt or solvate thereof. The process comprises the step of cleaving an $\epsilon$-amino protecting group $P\epsilon$ from a Degarelix precursor according to formula $(P_4)(P\epsilon)AA_1$-$AA_{10}$ in an organic solution comprising the precursor and a cleaving agent dissolved therein.

In this case, $P\epsilon$ is any side chain protecting group known in the art such as those described in E. Gross & J. Meienhofer, The Peptides: Analysis, Structure, Biology, Vol. 3: Protection of Functional Groups in Peptide Synthesis (Academic Press, N.Y., 1981), Suitable examples include 9-fluorenylmethyloxycarbonyl (Fmoc), CBZ, and substituted CBZ, such as, e.g., p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; aliphatic urethane-type protecting groups, such as t-butyloxycarbonyl (Boc), t-amyloxycarbonyl, isopropyloxycarbonyl, 2-(p-biphenylyl)-isopropyloxycarbonyl, and the like; cycloalkyl urethane-type protecting groups, such as cyclopentyloxycarbonyl, adamantyloxycarbonyl, and cyclo hexyloxycarbonyl; allyloxycarbonyl (Mac). Preferred protecting groups are Fmoc, Boc and Alloc with Fmoc being most preferred.

If required, the hydroxyl group of Ser may also be protected, although this is not preferred. In this case, $P_4$ is not hydrogen, but a hydroxyl protecting group such as for example, a $C_4$-$C_6$ alkyl (e.g. t-butyl, cyclohexyl), trityl, benzyl, a benzyl ether such as p-methoxybenzyl, or other substituted benzyls such as p-nitrobenzyl, p-chlorobenzyl, o-chlorobenzyl, 2,6-dichlorobenzyl, or (ψPro), (pseudoproline). If Ser is protected, particularly preferred is t-butyl, benzyl and 9-fluorenylmethyl ethers, t-butyl being most preferred. P4 is H, tBu, or (ψPro), preferably tBu or (ψPro), The cleaving agent used to remove the ε-amino protecting group or the Ser hydroxyl protecting group depends on the nature of the protecting group and are well known in the art. In a preferred embodiment, the same cleaving agent is used for both the ε-amino protecting group and the Ser hydroxyl protecting group, if present.

Preferred cleaving agents for the Ser hydroxyl protecting group are:
- trifluoracetic acid (TFA), HCl, or methanesulfonic acid, particularly for t-butyl ether as a protecting group
- $H_2$/Pd—C, HF, or trifluoromethane sulfonic acid, particularly for benzyl ether as a protecting group, and
- $SiCl_4$/anisol, particularly for 2-(methylsulfinyl)benzylether as a protecting group;

Preferred cleaving agents for the ε-amino protecting group are:
- trifluoracetic acid (TFA), HCl, or methanesulfonic acid, particularly for t-butyl carbamates as protecting group
- $H_2$/Pd—C, HF, or trifluoromethane sulfonic acid, particularly for benzyl carbamates as protecting group, and
- Piperidine, DBU and DEA, particularly for Fmoc as protecting group Preferred solvents include DCM, DMF, NMP, dioxane, EtOH, Neat HF, and TFA, Particularly preferred are the different cleavage conditions indicated in the following table 1:

Typically, a cleaving agent such as piperidine is dissolved in an organic solvent such as DMF, NMP under an inert atmosphere such as $N_2$ or argon and cooled to a temperature between −20 and 0° C., preferably −10 and −2° C., e.g. about −5° C. The protected intermediate (Pε)$AA_1$-$AA_{10}$ is added and the reaction mixture is then stirred at a temperature of between −20 and 25° C., preferably −10 and 10° C. and more preferably 0 and 5° C. When the protecting group has been removed (preferably the yield is >95% yield, most preferably >99%), the crude Degarelix can be precipitated, filtered and then washed with ether. For example, the crude Degarelix can be precipitated by adding it to ether, such as methyl t-butyl ether (MTBE) or DIPE, and stirring for 10 to 30 minutes. The precipitate can then be washed with ether (preferably DIPE). Subsequently, the solid may be taken up in e.g. ethyl acetate and stirred for some time at room temperature. The fine solid obtained may then be filtered, washed (e.g. with ethyl acetate) and dried under vacuum.

It has been found that extended reaction periods are not detrimental to the quality of the reaction and that no significant (<0.03% yield as determined by HPLC) increase in hydantoin impurity is observed if the reaction is allowed to proceed for up to 24 hours. Furthermore, particularly in the case of piperidine as a cleaving agent, no hydantoin impurity is observed if the reaction is performed in the presence of 5 Vol % water per volume of solvent (e.g. 0.1 ml of water per 2 ml solvent such as DMF) for up to 20 hours. This demonstrates the robustness of this deprotecting reaction for the PPS of Degarelix.

TABLE 1

Cleavage conditions

| Abbreviation | Name | Protected group | Cleavage reagent | Solvent |
| --- | --- | --- | --- | --- |
| t-Bu | t-Butyl ethers and esters | —OH and —$CO_2$H | TFA<br>HCl<br>Methanesulfonic acid | DCM<br>Dioxane<br>DCM |
| Bzl | Benzyl ethers and esters | —OH and —$CO_2$H | $H_2$/Pd—C<br>HF<br>Trifluoromethane-sulfonic acid | EtOH/water<br>Neat<br>DCM |
| MsOb | 4-(Methylsulfinyl)-benzyl ether | —OH | $SiCl_4$/anisol | TFA |
| Tce | 2,2,2-Trichloroethyl esters | —$CO_2$H | Zn | AcOH/$H_2O$ |
| Cbz or Z | Benzyloxycarbonyl | —$NH_2$ | $H_2$/Pd—C<br>HF<br>Trifluoromethane-sulfonic acid | EtOH/Water/acid<br>Neat<br>DCM |
| Boc | tert-Butoxy-carbonyl | —$NH_2$ | TFA<br>HCl<br>Methanesulfonic acid | DCM<br>Dioxane<br>DCM |
| Fmoc | 9-Fluorenylmethoxy-carbonyl | —$NH_2$ | piperidine<br>DBU (1,8-diazabicyclo[5.4.0]-undec-7-ene)<br>DEA (diethylamine) | DMF<br>DMF<br>DMF |
| Trt | Trityl (Trt) | —OH<br>—$NH_2$ | 1% TFA—DCM | DCM |
| TBDMS | Tert-butyl-dimethyl-silyl | —OH | TFA<br>ACOH—THF—$H_2O$ (3:1:1), 18 h<br>0.1 MTBAF in THF | THF |
| Cyclohexyl (CHX or $CH_x$) | Cyclohexyl | —OH | HF or TFSMA | Neat HF or DCM |
| Troc | 2,2,2-Trichloroethoxy-carbonyl | —$NH_2$ | Zn | AcOH/$H_2O$ |

Reference: Chem. Rev. 2009, 109, 2465-2504 (by Albert Isidro-Llobet et al.)

4+6 coupling and 3+7 coupling

In a second aspect, the invention relates to a liquid-phase process for preparing the protected Degarelix precursor having the formula $(P_4)(P\epsilon)AA_1-AA_{10}$ or a pharmaceutically acceptable salt or solvate thereof. This process may comprise the step of coupling a tetrapeptide intermediate according to formula $(P_4)Ac-AA_1-AA_4$ with a hexapeptide intermediate according to formula $(P\epsilon)AA_5-AA_{10}$. It may also comprise the step of coupling a tripeptide intermediate according to formula $Ac-AA_1-AA_3$ with a heptapeptide intermediate according to formula $(P_4)(P\epsilon)AA_4-AA_{10}$. In either case, the protecting group $P\epsilon$ may be any $\epsilon$-amino protecting group as discussed previously. The hydroxyl group of Ser may also be protected if required (i.e., in this case P4 is not hydrogen, but a hydroxyl protecting group). The coupling reaction is performed in an organic solution where the two peptides, a peptide coupling reagent and an organic amine base are dissolved therein. A peptide coupling additive may also be present.

The organic solvent, peptide coupling reagent, peptide coupling additive and organic amine base may be any of those known in the art of LPPS.

Typical organic solvents are THF, NMP (N-methylpyrrolidone), Davi, DMF, DMSO, and mixtures thereof.

Typical peptide coupling reagents are one or more of o-(7-azabenzotriazol-1-yl)-1,1,3,3-tetramethyluronium hexafluorophosphate (HATU), o-(benzotriazol-1-0)-1,1,3,3-tetramethyluronium hexafluorophosphate (HBTU), o-(benzotriazol-1-yl)-1,1,3,3-tetramethyluronium tetrafluoroborate (TBTU), benzotriazole-1-yl-oxy-tris(dimethylamino)phosphonium hexafluorophosphate (BOP), benzotriazole-1-yl-oxy-tris-pyrrolidinophosphonium hexafluorophosphate (PyBOP), N,N-bis-(2-oxo-3-oxazolidinyl)phosphonic dichloride (BOP—Cl), bromo-tris-pyrrolidino-phosphonium hexafluorophosphate (PyBroP), iso-butylchloroformate (IBCF), 1,3 dicyclohexylcarbodiimide (DCC), 1,3-diisopropyl-carbodiimide (DIC), 1-(dimethylaminopropyl)-3-ethylcarbodiimide hydrochloride (WSCDl), N-ethoxycarbonyl-2-ethoxy-1,2-dihydroquinoline (EEDQ), isopropylchloroformate (IPCF), 2-(5-norbornen-2,3-dicarboximido)-1,1,3,3-tetramethyluronium tetrafluoroborate (TNTU), propane phosphonic acid anhydride (PPAA) and 2-succinimido-1,1,3,3-tetramethyluronium tetrafluoroborate (TSTU). Preferred coupling reagents are DIC, HATU, HBTU, and BOP.

Typical peptide coupling additives are 3,4-dihydro-3-hydroxy-4-oxo-1,2,3-benzotriazine (HOOBt), 1-hydroxy-1H-benzotriazole (HOBt), 6-chloro-HOBt, and 1-hydroxy-7-azabenzotriazole (HOAt). Particularly preferred are HOBt and HOAt.

Typical organic amine bases are NMM, DIPEA, TEA, and collidine. Particularly preferred is DIPEA.

Particularly preferred is the combined use of HATU, HOAt, and DIPEA. Another preferred embodiment relates to the combined use of DIC, 6-chloro-HOBt, optionally in combination with copper salts.

Surprisingly, it has been found that the choice of organic solvent, peptide coupling reagent/additive and organic amine base has an effect on the yields of the desired products and on the racemisation of the Ser amino acid in the polypeptide backbone.

For instance, while THF, NMP, DCM, DMF and mixtures thereof can be used as solvents for these coupling reactions, the use of DMF, either alone or in a mixture (e.g. with DCM), increases the yield of the desired final product while at the same time reducing any D-Ser impurity. The use of DMF apparently increases the yield and reduces D-Ser impurities. The activation is rapid in a polar solvent such as DMF but slow in a non-polar solvent such as DCM. The HATU/HOAt combination leads to a highly efficient coupling partly because of rapid activation by a base such as DIEA or NMM followed by rapid coupling in the presence of the same base in a polar solvent like DMF. The effect of different solvents is illustrated in Table 2.

TABLE 2

Screening of different solvents during the coupling of AA1-AA4 and AA5-AA10 segment

| | | Coupling | | Purity by HPLC (%) | | |
| --- | --- | --- | --- | --- | --- | --- |
| Entry | Solvent | Reagent & additive | Yield (%) | Product CDEG-1 | Impurity (D-ser) | Remarks |
| 1 | THF | EDC•HCl | 35 | 62.42 | 16.29 | NMM as a base; CLEU-15 content 26.5% |
| 2 | NMP | EDC•HCl | 35 | 62.42 | 16.29 | NMM as a base; CLEU-15 content 0.17% |
| 3 | DCM-DMF | EDC•HCl | 53 | 47.81 | 10.39 | CLEU-15 content 25.54% |
| 4 | DMF | EDC•HCl | 65 | 72 | 9.2 | Collidine as a base |
| 5 | DMF | HATU/HOAt | 74 | 84.4 | 1.91 | 3.0 eq. of DIEA is used |
| 6 | DMF | HATU/HOAt | 74 | 85.3 | 1.44 | 3.0 eq. of DIEA is used |
| 7 | DMF | HATU/HOAt | 87 | 83.65 | 1.44 | 3.0 eq. of DIEA is used |

The choice of coupling reagent and additive also has a large effect on the yield and degree of racemisation. Coupling reactions using HBTU, HCTU, TBTU, BOP and HATU were performed and found with HBTU and HATU giving the best overall yields. However, it was found that coupling reactions using BOP or HATU as coupling reagent led to much less racemisation of the Ser amino acid.

The addition of a coupling additive significantly improves the yield of the desired polypeptide. In many cases the coupling additive also reduces the degree of racemisation of the Ser amino acid even further thus leading to a product with fewer impurities. Combinations of coupling reagent and additive which increased yield are TBTU/HOAt, HATU/HOAt and HATU/HOBt. Surprisingly, the combination of TBTU/HOAt or HATU/HOAt increased yield while at the same time reducing racemisation, with HATU/HOAt performing best out of all the combinations tested.

The effect of different coupling agents and additives is illustrated in the following Tables 3 and 4.

TABLE 3

Screening of different coupling reagents to control the racemization

| Entry | Base | Coupling Reagent & additive | CDEG-1 Yield (%) | Purity by HPLC (%) CDEG-1 | Impurity (D-ser) | Remarks |
|---|---|---|---|---|---|---|
| 1 | NMM | EDC•HCl/HOBt | 67 | 65 | 20 | Racemization is more |
| 2 | NMM | EDC•HCl/HOBt | 67 | 65 | 18.9 | Racemization is more |
| 3 | DIEA | TBTU | 39 | 67.93 | 13.34 | 1.3% of CLEU-15 remains |
| 4 | DIEA | HBTU | 53 | 54.9 | 20.49 | 1.9% of CLEU-15 remains |
| 5 | DIEA | EDC•HCl | 51 | — | — | 68.9% of CLEU-15 remains |
| 6 | NMM | HBTU | 78 | 61.42 | 15.16 | 9.8% of CLEU-15 remains |
| 7 | NMM | HCTU | 60 | 51.63 | 15.92 | 7.32% of CLEU-15 remains |
| 8 | NMM | TBTU | 53 | 62.78 | 14.73 | 3.75% of CLEU-15 remains |
| 9 | NMM | BOP | 51 | 46.3 | 8.92 | 11.93% of CLEU-15 remains |
| 10 | NMM | HATU | 74 | 65.97 | 10.62 | 4.52% of CLEU-15 remains |
| 11 | DIEA | TBTU/HOAt | 98 | 76.26 | 6.8 | 0.14% of CLEU-15 remains |
| 12 | DIEA | DIC/HOAt | — | 20.49 | 1.18 | 45.9% of CLEU-15 remains |
| 13 | DIEA | HATU/HOAt | 74 | 83.16 | 2.9 | No unreacted CLEU-15 |
| 14 | NMM | HATU/HOAt | 81 | 64.0 | 13.32 | 7.1% of CLEU-15 remains |
| 15 | NMM | HATU/HOBt | 89 | 65.0 | 13.14 | 4.35% of CLEU-15 remains |
| 16 | NMM | EDC•HCl/HOAt | 74 | 70.38 | 13.66 | No unreacted CLEU-15 |
| 17 | DIEA | HATU/HOAt | 79 | 79.79 | 2.3 | This reaction was repeated in larger scale |
| 18 | DIEA | TBTU/HOAt | 84 | 75.8 | 7.2 | Reaction was repeated in larger scale. |
| 19 | DIEA | HATU/HOAt | 74 | 84.4 | 1.91 | Reaction was repeated in larger scale. |
| 20 | DIEA | HATU/HOAt | 74 | 85.3 | 1.44 | Reaction was repeated in larger scale. |
| 21 | DIEA | HATU/HOAt | 87 | 84 | 1.44 | Reaction was repeated in larger scale. |
| 22 | DIEA | HATU/HOAt | 79 | 84.5 | 1.37 | Reaction was repeated in larger scale. |

TABLE 4

Screening of different additives to control the racemization during the coupling of AA1-AA4 and AA5-AA10 segment

| Entry | Coupling Reagent | Additive | Base | CDEG-1 Yield (%) | Purity by HPLC (%) CDEG-1 | (D-ser) | Remarks |
|---|---|---|---|---|---|---|---|
| 1 | TBTU | HOAt | DIEA | 98 | 76.26 | 6.8 | 0.14% of CLEU-15 remains |
| 2 | DIC | HOAt | DIEA | — | 20.49 | 1.18 | 45.9% of CLEU-15 remains |
| 3 | HATU | HOAt | DIEA | 74 | 83.16 | 2.9 | Completion of reaction |
| 4 | HATU | HOAt | NMM | 80 | 64.0 | 13.32 | 7.1% of CLEU-15 remains |
| 5 | HATU | HOBt | NMM | 89 | 65.0 | 13.14 | 4.3% of CLEU-15 remains |
| 6 | EDC•HCl | HOAt | NMM | 74 | 70.38 | 13.66 | No unreacted CLEU-15 |
| 7 | HATU | HOAt | DIEA | 79 | 79.79 | 2.3 | Repeat reaction |
| 8 | TBTU | HOAt | DIEA | 84 | 75.8 | 7.2 | Repeat reaction |
| 9 | HATU | HOAt | DIEA | 74 | 84.4 | 1.91 | 3.0 eq. of base is used |
| 10 | HATU | HOAt | DIEA | 74 | 85.3 | 1.44 | 3.0 eq. of base is used |
| 11 | HATU | HOAt | DIEA | 87 | 83.65 | 1.44 | 3.0 eq. of base is used |
| 12 | EDC•HCl | HOBt | NMM | 67 | 65 | 20 | Racemization is more |
| 13 | EDC•HCl | HOBt | NMM | 64 | 65 | 17.9 | Racemization is more |
| 14 | EDC•HCl | HOBt | NMM | 67 | 65 | 18.9 | Racemization is more |
| 15 | | HOSu | NMM | — | — | — | Reaction did not proceed |

The choice of organic amine base also affects the reaction. For the present invention, NMM and DIEA are preferred as they allow the desired polypeptide to be obtained in the best yields. DIEA is more preferred since this base reduces the degree of Ser racemisation. It has also been found that the amount of base affects the reaction. When a base such as DIEA is used, it was found that the more base present, the lower the yield and higher the degree of racemisation. For example, six equivalents of base (with respect to A51-A10) lead to a two-fold increase of the racemisation product as when three equivalents of base are used. Thus, it is preferred to use 1-5 equivalents of base, more preferably 2-4 equivalents of base and most preferably 2.5 to 3.5 equivalents of base in these coupling reactions. The effect of different bases and their amounts is shown in the following tables 5 and 6.

TABLE 5

Screening of different bases to control the racemization during the coupling of AA1-AA4 and AA5-AA10 segment

| Entry | Coupling Reagent | Additive | Base | Yield (%) CDEG-1 | Purity by HPLC (%) CDEG-1 | (D-ser) | Remarks |
|---|---|---|---|---|---|---|---|
| 1 | TBTU | HOAt | DIEA | 98 | 76.26 | 6.8 | 0.14% of CLEU-15 remains |
| 2 | DIC | HOAt | DIEA | — | 20.49 | 1.18 | 45.9% of CLEU-15 remains |
| 3 | HATU | HOAt | DIEA | 74 | 83.16 | 2.9 | No CLEU-15 remains |
| 4 | HATU | HOAt | NMM | 80 | 64.0 | 13.32 | 7.1% of CLEU-15 remains |
| 5 | HATU | HOBt | NMM | 89 | 65.0 | 13.14 | 4.35% of CLEU-15 remains |
| 6 | EDC•HCl | HOAt | NMM | 74 | 70.38 | 13.66 | No CLEU-15 remains |
| 7 | HATU | HOAt | DIEA | 79 | 79.79 | 2.3 | |
| 8 | TBTU | HOAt | DIEA | 84 | 75.8 | 7.2 | |
| 9 | HATU | HOAt | DIEA | 74 | 84.4 | 1.91 | 3.0 eq. of base is used |
| 10 | HATU | HOAt | DIEA | 74 | 85.3 | 1.44 | 3.0 eq. of base is used |
| 11 | HATU | HOAt | DIEA | 87 | 83.65 | 1.44 | 3.0 eq. of base is used |
| 12 | EDC•HCl | HOBt | Collidine | 65 | 72 | 9.2 | |
| 13 | EDC•HCl | HOBt | NMM | 67 | 65 | 20 | Racemization is more |
| 14 | EDC•HCl | HOBt | NMM | 64 | 65 | 17.9 | Racemization is more |
| 15 | EDC•HCl | HOBt | NMM | 67 | 65 | 18.9 | Racemization is more |

TABLE 6

Screening of base equivalence to control the racemization during the coupling of AA1-AA4 and AA5-AA10 segment

| Entry | DIEA Qty (eq.) | Coupling Reagent & additive | CDBG-1 Yield (%) | Purity by HPLC (%) Product CDEG-1 | Impurity (D-ser) |
|---|---|---|---|---|---|
| 1 | 6.0 | HATU/HOAt | 62 | 74.19 | 1.5 |
| 2 | 5.0 | HATU/HOAt | 69 | 79.00 | 3.88 |
| 3 | 4.5 | HATU/HOAt | 68 | 84.12 | 1.18 |
| 4 | 4.0 | HATU/HOAt | 70 | 82.64 | 1.19 |
| 5 | 3.0 | HATU/HOAt | 74 | 84.4 | 1.91 |
| 6 | 3.0 | HATU/HOAt | 74 | 85.3 | 1.44 |
| 7 | 3.0 | HATU/HOAt | 87 | 83.65 | 1.44 |

The temperature that the coupling reaction is performed also influences the yield and the degree of racemisation of the final product. It was found that a reaction carried out at −15° C. gives higher yield, higher purity and less racemisation of the final product than the equivalent reaction carried out at −5° C. Thus, it is preferable to carry out these coupling reactions at temperatures lower than −5° C., preferably lower than −10° C. and most preferably at −15° C. or lower. The reaction time of these coupling reactions is usually 2-3 hours.

It should be noted that by controlling the reaction temperature and the amount of base added, it is also possible to reduce any hydantoin impurity formation. The hydantoin content is preferably less than 0.5 wt. %, more preferably less than 0.3 wt. %. Thus, it is preferred to use 2.5 to 3.5 equivalents of base at temperatures of −10° C. or lower in these reactions.

Finally, the order of addition of the various reagents also plays a role in the final yield, purity and amount of racemisation. If the peptides and coupling additive are first dissolved in the organic solvent before the coupling reagent and the organic amine are added, the overall yield of the desired product is significantly higher. Furthermore, the amount of racemisation is drastically reduced.

Fragment $(P_4)Ac-AA_1-AA_4$

The present invention provides different methods for preparing $(P_4)Ac-AA_1-AA_4$.

In a third aspect, the invention relates to a liquid-phase process for preparing a Degarelix intermediate having the formula $(P_4)Ac-AA_1-AA_4$:

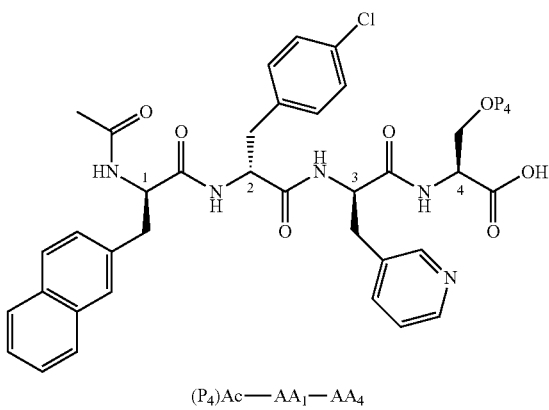

$(P_4)Ac—AA_1—AA_4$ or a pharmaceutically acceptable salt or solvate thereof, wherein $P_4$ is hydrogen or a hydroxyl-protecting group, preferably hydrogen.

When preparing $(P_4)Ac-AA_1-AA_4$, an ester having the formula $(P_4)Ac-AA_1-AA_4-R$ is first prepared, wherein R is a carboxyl protecting group, such as a benzyl group, preferably however a $C_1$-$C_4$ alkyl group. Normally, a benzyl ester of serine is used, the benzyl group being then removed by hydrolysis with tetrabutylammonium hydroxide (see for example WO 99/26964). However, it was found that in the preparation of Degarelix, the tetrabutylammonium ions were not removed completely during subsequent operations and were carried through to the final product. This problem was overcome by using a $C_1$-$C_4$ alkyl ester of serine (e.g. serine methyl ester). It was found that the alkyl ester could be easily hydrolyzed using an alkali hydroxide such as LiOH. The yield and quality of the tetrapeptide was not affected by this change and the problem of tetrabutylammonium ion impurities was eliminated.

For example, a compound according to formula $(P_4)$Ac-$AA_1$-$AA_4$-R may be suspended in an organic solvent such as THF and then stirred and cooled to a temperature of between −20 and 5° C., and more preferably −5 and 0° C. An aqueous solution of LiOH is then added to the cooled solution. The aqueous LiOH is added at a rate that maintains the temperature of the cooled solution in the range of −5 to 0° C. or below. The solution (oftentimes turbid) is stirred for up to 12 hours, preferably up to 3 hours, before being added, with good stirring, to water with a temperature of 5° C. or below, or preferably a mixture of ice and water. Any precipitate at this point is removed by filtration. The pH is then adjusted to pH 4.1-4.3, preferably about 4.2 using any known pH adjusting agent. Preferred is HCl, for example 2M HCl. The precipitate that forms after adjusting the pH is collected by filtration. The precipitate can be further purified by washing it with water, and/or stirring a slurry of it in refluxing MeOH and/or a MeOH/MeCN mixture before collecting it by filtration and then drying it to yield $(P_4)$Ac-$AA_1$-$AA_4$.

A fourth aspect of the invention concerns a process for preparing the compound $(P_4)$Ac-$AA_1$-$AA_4$-R by coupling Ac-$AA_1$-$AA_3$ with $(P_4)AA_4$-R or coupling Ac-$AA_1$-$AA_2$ with $(P_4)AA_3$-$AA_4$-R, wherein R is a $C_1$-$C_4$-alkyl and $P_4$ is hydrogen or a hydroxyl-protecting group, preferably hydrogen. For the coupling reaction, essentially the same reagents and conditions as those described above can be used.

In a fifth aspect, this invention relates to a solid-phase process for preparing a Degarelix intermediate having the formula (P4)Ac-$AA_1$-$AA_4$:

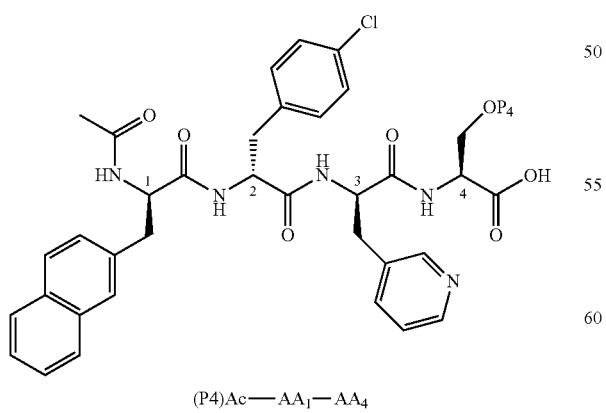

(P4)Ac—$AA_1$—$AA_4$ or a pharmaceutically acceptable salt or solvate thereof, comprising the steps:

a) reacting (PN)AA2 with (P4)AA₃— AA₄—RESIN to provide (P4, PN)AA₂— AA₄—RESIN;

b) removal of PN from (P4, PN)AA₂— AA₄—RESIN to provide (P4)AA₂— AA₄—RESIN;

c) reacting (PN)AA1 with (P4)AA₂— AA₄—RESIN to provide (P4, PN)AA₁— AA₄—RESIN;

d) if PN is not acetyl, removal of PN from (P4, PN)AA₁— AA₄—RESIN to provide (P4)AA₁— AA₄—RESIN and subsequently acetylating (P4)AA₁— AA₄—RESIN to provide (P4)Ac— AA₁— AA₄—RESIN;

and
e) cleaving (P4)Ac— AA₁— AA₄—RESIN to provide (P4)AC-$AA_1$-$AA_4$.
wherein P4 is H or a hydroxyl protecting group on AA4, and PN is an amino protecting group.

PN is preferably Fmoc, which is preferably removed with piperidine/NMP.

P4 is preferably tBu or (ΨPro). Particularly preferred is the combination of (ψPro) for P4 and Fmoc for PN.

Each coupling step is preferably carried out in a manner known per se, preferably however using HATU (or HBTU) and DIPEA and coupling additives.

The starting material (P4)AA$_3$—AA$_4$—[RESIN]

starting can be prepared by coupling (PN, P4)AA$_3$-AA$_4$ to a resin, for example to a 2-ClTrt resin, and then removing PN, or by coupling (PN, P4)AA$_4$ to

[RESIN]

to obtain (PN, P4)AA$_4$—[RESIN], removing PN, and then reacting (PN)AA$_3$ with (P4)AA$_4$—[RESIN]

to provide (PN, P4)AA$_3$—AA$_4$—[RESIN], and then removing PN. This is illustrated in FIGS. 4 and 5.

Suitable resins ([RESIN])

include trityl, 2-ClTrt and SASRIN.

In the case P4 is (ψPro) and PN is Fmoc, (PN, P4)AA$_3$-AA$_4$ can be prepared following J. Am. Chem. Soc. 1996, 118, 9218-9227. That is, Fmoc protected AA3 is activated; reacted with serine or a salt thereof, and subsequently reacted with acetone or acetone dimethylketal, as illustrated below. Fmoc-D3 PaI-Ser(($\psi^{Me,Me}$Pro)-OH is particularly preferred as (PN, P4)AA$_3$-AA$_4$.

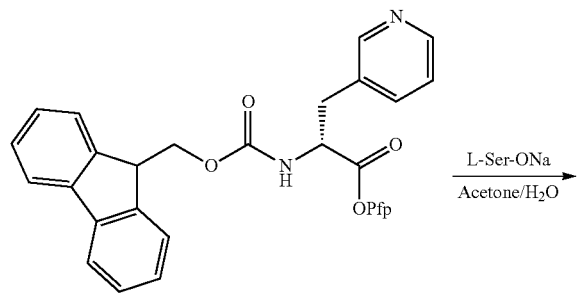

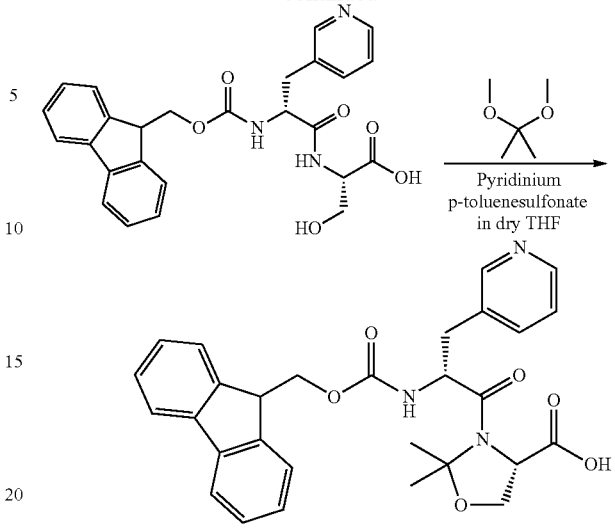

Fmoc-D3PaI-Ser($\psi^{Me,\,Me}$Pro)-OH

Fragment (P$_X$)(Pϵ)AA$_5$-AA$_{10}$NH$_2$

A sixth aspect of the invention concerns liquid-phase process for preparing the hexapeptide (Pϵ)AA$_5$-AA$_{10}$NH$_2$ comprising the coupling of (Pϵ)AA$_6$-AA$_{10}$NH$_2$ and (P$_X$)AA$_5$, wherein P$_X$ is an amino protecting group and AA5 to AA10 and Pϵ have the same meaning as above, to provide (P$_X$)(Pϵ)AA$_5$-AA$_{10}$NH$_2$, and cleaving Px with TFA to provide (Pϵ) AA$_5$-AA$_{10}$NH$_2$.

A seventh aspect of the invention concerns a liquid-phase process for preparing the hexapeptide (Pϵ)AA$_5$-AA$_{10}$NH$_2$ by coupling (P5)AA$_5$-AA$_7$ with (Pϵ)AA$_8$-AA$_{10}$NH$_2$ to provide (P5, Pϵ)AA$_5$-AA$_{10}$NH$_2$, and subsequently cleaving P5 to provide (Pϵ)AA$_5$-AA$_{10}$NH$_2$ (wherein P5 is an amino-protecting group on AA5).

P5 protecting group is preferably BOC. Pϵ is preferably 9-fluorenylmethyloxycarbonyl (Fmoc). The coupling reaction is preferably carried out in the presence of HATU.

(P5)AA$_5$-AA$_7$ and (Pϵ)AA$_5$-AA$_{10}$NH$_2$ are preferably synthesized by solid phase peptide synthesis, e.g. as illustrated in FIGS. 6 and 7, respectively. The following combinations of P5 and Pϵ are preferred:

| P5 | Pϵ |
|---|---|
| Boc | Fmoc |
| Cbz | Boc |
| Troc | Boc |

That is, (P5)AA$_5$-AA$_7$OH can be prepared by coupling protected AA7 to a resin; removing the protecting group (e.g. Fmoc); reacting protected AA6 with the obtained product; removing the protecting group (e.g. Fmoc); reacting protected AA5 (e.g. BOC protected) with the obtained product; and cleavage from the resin. This is illustrated in FIG. 6.

(Pϵ)AA$_5$-AA$_{10}$NH$_2$ can be prepared by coupling protected AA10 to a resin, e.g. a Rink amide resin; removing the protecting group (e.g. Fmoc); reacting protected AA9 with the obtained product; removing the protecting group (e.g. Fmoc); reacting protected AA8 (preferably Boc-protected on the alpha-amino group and Fmoc-protected on the side chain)

with the obtained product; removing the alpha-amino protecting group; and cleavage from the resin. This is illustrated in FIG. 7.

(Pε)AA$_8$-AA$_{10}$NH$_2$ can also be prepared by reacting AA10 NH$_2$ with protected (e.g. BOC) AA9; removing the protecting group; reacting AA9-AA10 NH$_2$ with protected AA8 (preferably Boc-protected on the alpha-amino group and Fmoc-protected on the side chain); and removing the protecting group on the alpha-amino group.

In an eighth aspect, the invention relates to the purification of Degarelix. The purification can be carried out in a manner known to the skilled person, e.g. by preparative chromatography.

For example, first purification of Degarelix is achieved with a PLRP—S stationary phase, pH 2.25 using TEAP as a buffer and MeCN (75:25) as mobile phase. Purity of up to 95% can be obtained with this step. If required, a second purification can be carried out using a combination of C8 and C18 columns (e.g. Zorbax) to achieve purity of 99% and above.

EXPERIMENTAL

The following examples are intended to illustrate a process for the LPPS synthesis of Degarelix. Reference is made to FIGS. 1 and 2 for the structures of each peptide and polypeptide described herein.

CLEU-2:

L-Cbz-proline (50.0 g) was dissolved in 2-propanol (500 ml≙10 V) and the solution was cooled to 15° C. N-Methylmorpholine (25 ml≙0.5 V) was then added slowly. After stirring the solution for 15 minutes, 28.49 g (1.04 eq.) iso-butyl chloroformate was added dropwise at −15° C. A solution of D-ala-NH$_2$.HCl (27.48 g, 1.1 eq) and NMM (25 ml≙0.5 V) in water (250 ml≙5 V) was added to the reaction mixture at −15° C. The mixture was stirred for 30 minutes at the same temperature and then warmed to 25° C. and stirred for 3-5 hrs. The reaction mixture was quenched by adding ethyl acetate (1000 ml≙20 V) and water (10 V) containing NaCl (25 g) and NaHCO$_3$ (25 g). The organic layers were separated, washed with water (2×500 ml≙10 V) and then dried over sodium sulphate. The organic layer was concentrated to 4 volumes under vacuum below 40° C. The solution was diluted with ethyl acetate (250 ml≙5 V) and n-hexane (375 ml≙7.5 V) was added dropwise to obtain a white solid. The solid was filtered off and dried to afford the product.

Output: 35.2 g; 54.7%; [α]$_{25}^D$: −13.0° [CHCl$_3$, Literature report: −11.2° (U.S. Pat. No. 5,710,246)]). HPLC purity: 99.44%

CLEU-4:

CLEU-2 (19.5 g) was taken in 2-propanol (129 ml≙6.5 V) into a Parr hydrogenation flask and a solution of p-toluene-suiphanic acid in water (20 ml≙1.0 V) was added to it. 10% Pd/C (5% w/w) was added to the reaction mixture and the mixture then hydrogenated at 40 psi for 2 hrs. When TLC showed the disappearance of the starting material, the catalyst was filtered and washed with 2-propanol (79 ml≙4 V) and water (8.75 ml≙0.5 V). The filtrate was concentrated under vacuum and stripped off with acetonitrile (4×254 ml≙13 V). The residue was taken in a flask and acetonitrile (215 mL≙11 V) was added followed by Boc-Lys(Cbz)-OH (25.5 g≙1.1 equiv) and HOBt (9.9 g≙1.2 equiv). The suspension was cooled to −5° C. and NMM (14.95 g≙2.45 equiv) was added slowly. Finally, a solution of EDC.HCl (15.3 g≙1.3 equiv) in acetonitrile (120 ml≙6 V) was added. The reaction mixture was then warmed to 25° C. and stirred for 10-12 hrs at the same temperature. The solvent was removed under vacuum below 40° C. and diluted with water (120 ml≙6 V). The product was extracted with ethyl acetate (878 ml≙45 V), water (120 ml≙6 V), and 10% sodium carbonate (110 ml≙5.7 V). The aqueous layer was extracted with ethyl acetate (2×430 ml≙2×22 V) and the organic layers combined and washed with 10% citric acid solution (2×105 ml), 10% sodium carbonate solution (2×110 ml≙2×5 V), water (120 ml≙6 V) and dried over sodium sulphate. The organic layer was concentrated to 10-12 volumes under vacuum below 40° C., stripped off with ethyl acetate (3×20 V) and maintained the final 10-12 volumes in each stripping. N-hexane (14 V) was added dropwise to the concentrate mass to get a white solid. The solid was filtered off and dried to afford the product.

Output 29.2 g; Yield: 86.6%; Purity 99.18%, [α]$_{25}^D$: −26.0° (c 1, CHCl$_3$)

CLEU-5:

CLEU-4 (16.3 g) was taken in a mixture of methanol (163 ml≙10 V), acetone (22 ml≙1.4 V) in a stainless steel Parr hydrogenation flask. 10% Pd/C (10% w/w) was added and the mixture was hydrogenated (60 psi) for 8-12 hrs at 25° C. After the starting material had disappeared (TLC), the catalyst was filtered through celite and was washed with methanol (163 ml≙10 V). The filtrate was concentrated under vacuum below 40° C. and the residue was stripped off with ethyl acetate (3×143 ml≙3×9 V). The residue was then taken in ethyl acetate (51 ml≙3 V) and n-hexane (20.4 ml≙1.25 V) added. The mixture was stirred for 2-3 hrs to obtain a free solid. The solid was filtered, washed with n-hexane (38 ml≙2 V), and dried under vacuum below 40° C.

Output: 12.3 g; Yield: 90.8%; Purity: 98.9%

CLEU-6:

CLEU-5 (12.2 g) was added to THF (40 ml≙3.3 V) and the mixture was cooled to 0° C. 10% sodium carbonate solution (34 ml≙2.7 V) was added to the mixture over 20 minutes. Fmoc-Cl (8.63 g≙1.2 equiv) in THF (12.2 ml≙1.0 V) was then added slowly over 15-20 minutes at 0° C. The reaction mixture was stirred for 1 hr at same temperature and diluted with water (134.2 ml≙11 V). The product was extracted with ethyl acetate (269 ml≙22 V). The organic layer was washed with water (134.2 ml≙11 V), 10% citric acid solution (2×134 ml≙2×11 V) and water (134.2 ml≙11 V). The organic layer was concentrated under vacuum below 40° C. and the crude product was purified by column chromatography.

Output: 13.3 g; Yield: 73.2%; Purity: 98.2%

CLEU-7:

CLEU-6 (9.0 g) was charged to a TFA (61 ml≙6.75 V) and m-cresol (0.61 ml) solution at −5° C. The reaction mixture was stirred for 2 hrs at 0° C. and then concentrated under vacuum below 35° C. Traces of TFA were removed by co-distillation with toluene (2×45 ml). The product was crystallized from a mixture of MTBE (9 ml≙1 V), and DIPE (90 ml≙10 V). The solid was filtered off under nitrogen, washed with DIPE (180 ml≙20 V) and dried under vacuum to get pure CLEU-7.

Output: 8.8 g; Yield: 90.4%; Purity: 98.3%.

Comment: CLEU-7 material is hygroscopic in nature and thus should be handled with care.

CLEU-8:

CLEU-7 (8.5 g) was taken in acetonitrile (85 ml≙10 V). Boc-Leu-OH (3.12 g≙1.1, equiv), HOBt (2.31 g≙1.39 equiv) and NMM (1.4 ml≙1.03 equiv) were added to the solution. The solution was cooled to −2° C. and treated with NMM (1.4 ml≙1.03 equiv) and EDC.HCl (2.58 g≙1.1 equiv). The reaction mixture was stirred for 2-3 hrs at 0° C. and the solvent was removed by distillation under vacuum. 10% citric acid (85 ml≙10 V) and ethyl acetate (213 ml≙25 V) were added to the residue. The organic layer was separated and washed with 10% citric acid solution (2×85 ml≙2×10.0 V), DM water (85 ml≙10 V), and 5% sodium bicarbonate solution (3×85 ml≙3× 10.0 V) and again with DM water (85 ml≙10 V). Finally, the organic layer was dried over sodium sulphate and concentrated under vacuum below 35° C. to obtain the crude product. The crude product was crystallized from MTBE (68 ml≙8 V) and n-hexane (34 ml≙4 V). The solid was dried under vacuum at below 35° C.

Output: 7.8 g; Yield: 81.2%; Purity: 97.5%.

CLEU-9:

CLEU-8 (7.5 g) was charged to a TFA (54 ml≙7.2 V) and m-cresol (0.27 ml) solution at −5° C. The reaction mixture was stirred for 2.0 hrs at 0° C. and then concentrated under vacuum below 35° C. Traces of TFA were removed by co-distillation with toluene (2×38 ml the product was crystallized from MTBE (75 ml≙10 V) and n-hexane (413 ml≙15 V). The solid was filtered under nitrogen, washed with n-hexane (37.5 ml≙5 V), and dried under vacuum to yield pure CLEU-9.

Output: 7.2 g; Yield: 94.8%; Purity: 97.2%

CLEU-12:

CLEU-9 (10.5 g) was taken in acetonitrile (158 ml≙15 V) under nitrogen atmosphere. CMAP-5A (4.2 g≙1.0 equiv), HOBt (2.11 g≙1.2 equiv) were added into the suspension and the mixture was cooled to 0° C. EDC.HCl (2.73 g≙1.1 equiv) was added into the suspension followed by slow addition of NMM (1.38 g≙1.05 equiv). The reaction mixture was stirred for 0.5 hr at 0° C., warmed to ambient conditions and then stirring was continued for 3 hrs. The solvent was removed under vacuum below 35° C. and the residue was taken in a mixture of 10% citric acid (105 ml≙10 V) and ethyl acetate (263 ml≙25 V). The organic layer was separated and washed with 10% citric acid solution (105 ml≙10 V), DM water (105 ml≙10 V), 5% sodium bicarbonate solution (3×105 ml≙3×10 V), and DM water (105 ml≙10 V). The organic layer was dried over sodium sulphate and concentrated under vacuum below 35° C. The crude product was precipitated with n-hexane (84 ml≙8 V), washed with n-hexane (2×84 ml≙2×8 V), and dried under vacuum at 35° C.

Output: 10.5 g; Yield: 80.7%; Purity: 92.1%

CLEU-13:

CLEU-12 (10.5 g) was charged to a TFA (78.8 ml≙7.5 V) and m-cresol (0.4 ml) solution at −5° C. The reaction mixture was stirred for 2 hrs at 0° C. and then concentrated under vacuum below 35° C. Traces of TFA were removed by co-distillation with toluene (2×52 ml). The residue was taken up in ethyl acetate (105 ml≙10 V) and n-hexane (158 ml≙15 V) is added to precipitate the product. The solid was filtered off under nitrogen and washed with n-hexane (53 ml≙5 V). The compound was dried under vacuum at 35° C.

Output: 9.6 g; Yield: 90.5%; Purity: 91.9%.

CLEU-14:

CLEU-13 (9.5 g) was dissolved in DMF (95 ml≙10 V) under a nitrogen atmosphere. NMM (1.0 g≙1.05 equiv), CSER-2 (3.95 g≙1.0 equiv) and HOBt (1.4 g≙1.1 equiv) were added to the solution and the reaction mass was cooled to 0° C. EDC.HCl (2.0 g≙1.1 equiv) and NMM (1.0 g≙1.05 equiv) were added subsequently into the mixture. The reaction mass was stirred for 5 hrs at 0° C. and then poured into ice cooled water (950 ml≙100 V) and stirred for 30 minutes. The precipitated solid was filtered off and washed with water (20 V), 10% citric acid (10 V), again with water (190 ml≙20 V), 5% NaHCO₃ solution (95 ml≙10 V), and water (95 ml≙10 V). The product was dried under vacuum below 35° C.

Output: 10.3 g; Yield: 84.40%; Purity: 90.4%.

CLEU-15:

CLEU-14 (10.0 g) was charged to a TFA (75 ml≙7.5 g) and m-cresol (0.37 ml) solution at −5° C. The reaction mixture was stirred for 2 hrs at 0° C. and then concentrated under vacuum below 35° C. Traces of TFA were removed by co-evaporation with toluene (2×50 ml). The residue was taken up in ethyl acetate (100 ml≙10 V) and n-hexane (60 ml≙6 V) was added to precipitate the product. The solid was filtered off under nitrogen, washed with n-hexane (2×30 ml≙6 V) and then dried under vacuum at 35° C.

Output: 9.6 g; Yield: 95.0%; Purity: 91.5%.

CSER-2:

To a stirred solution of L-hydroorotic acid (23.4 g, 148 mmol) and N-hydroxysuccinimide (18.14 g≙1.1 equiv) in dry DMF (585 ml≙25 V) was added DIC (20.5 g≙1.1 equiv) with external ice water cooling. The reaction mixture was stirred at room temperature for 13-14 hrs. The precipitate was filtered off and the filtrate was evaporated. The oily residue was washed with diisopropyl ether (94 ml≙4 V) and dissolved in dry DMF (293 ml≙12.5 V). N-Boc-L-4-aminophenylalanine (41.5 g≙1.0 equiv) was added to the above solution. DIEA (22.97 g≙1.2 equiv) was added at 0° C. and the reaction mixture was stirred for 22 hrs and the solvent then evaporated. The residue was mixed with water (702 ml≙30 V) and the pH of the resulting suspension was adjusted to 9.0 with saturated sodium bicarbonate solution. The precipitate of diisopropylurea was filtered off and the filtrate was washed with ethyl acetate (70.2 ml≙3 V). The aqueous layer was acidified to pH 2.5 with 6 N HCl and the resulting precipitate collected by filtration. The product was obtained as a yellow solid.

Output: 40.0 g; Yield 64%; mp-270° C., $[\alpha]_{25}^D$=+61.5 (c 1.0, 1% NaHCO₃); Purity 95%.

CBBC-2B:

Fragment-A (20.0 g) (purchased from Chirotech, UK) was dissolved in DMF (300 ml≙15 V) at 30-35° C. and then cooled −10° C. to 5° C. wherein HOBt (5.06 g≙1.1 equiv) was added to the mixture, stirred for 30 minutes before L-serine methyl ester (5.29 g≙1.0 equiv) was added to the suspension. The mixture was stirred for 30 minutes, treated with NMM (7.23 g≙2.1 equiv) and then stirred for 30 minutes. EDC.HCl (7.18 g≙1.1 equiv) was then added to the suspension and the reaction mixture was stirred for 5 hrs at −5° C. to 0° C. The reaction mixture was poured into chilled DM water (151 or 1500 ml≙75 V) and stirred for 30 minutes. The product was precipitated by stirring at 0-5° C. After 1 hr the resulting solid was collected by filtration. The filter cake was washed with water (200 ml≙10 V), 10% citric acid (200 ml≙10 V), again with water (200 ml≙10 V), 5% NaHCO₃ solution (200 ml≙10 V), water (200 ml≙10 V) and then the solid was dried under vacuum for 4 hrs. The product was slurried in methanol (300 ml≙15 V) and stirred for 1 hr. The suspension was filtered and the cake washed with methanol (100 ml≙5 V) then dried under vacuum at 30-35° C. to a constant weight.

Output: 22 g; Yield: 93.8%.

CBBC-3B:

CBBC 2B (20.0 g) was suspended in THF (500 ml≙25 V) and then stirred and cooled to −5° C. to 0° C. To the cooled solution was added an aqueous solution of lithium hydroxide (3.65 g≙3.0 equiv) at such a rate that the reaction temperature was maintained at between −5° C. and 0° C. (about 30 mins). The solid dissolved after the base was added to afford a slightly turbid solution. Stirring was continued for another 2 hrs at below −5° C. to 0° C. After 3 hrs the turbid reaction mixture was added slowly, with good stirring, into ice/water (700 ml≙35 V) at 5° C. whereby any undissolved particles were filtered under vacuum. While stirring, the pH was adjusted to 4.2 using 2M HCl (≈40 ml≙≈2 V). The thick white precipitate was collected by filtration and the damp cake washed with 200 ml≙10 V of water, air dried under vacuum briefly, slurried in 400 ml≙20 V of methanol and then stirred under reflux. The suspension was filtered and the damp cake washed again with 200 ml 10 V of methanol then dried under vacuum. The wet cake was then taken in methanol (400 ml≙20 V) and acetonitrile (200 ml≙10 V) and stirred under reflux. The suspension was filtered hot and the damp cake washed with 200 ml≙10 V of methanol then dried under vacuum. The product was dried under vacuum at 35° C. to a constant weight to afford the tetrapeptide acid Ac-(AA$_1$-AA$_4$).

Output: 120 g; Yield: 62.0%; Purity: 97.1%.

CDEG-1:

CLEU-15 (4.3 g), CBBC-3A (2.24 g≙1.0 equiv), and HOAt (0.56 g≙1.2 equiv) were charged into an RBF containing DMF (~2.6 ml≙6 V). The mixture was stirred for 15-30 minutes to yield a clear solution at 25° C. and then treated with DIPEA (1.71 g≙4.0 equiv) The reaction was then cooled to −15° C. and HATU (1.57 g≙1.25 equiv) was added to the mixture. The reaction mixture was stirred for 2 hrs at −10° C., warmed to 20° C. and then stirred for 1 hr at the same temperature. The reaction mass was added to 10% citric acid solution (270 ml≙60 V) and stirred for 30 minutes at 10° C. The precipitated solid was filtered, washed with water (270 ml≙30 V), 5% NaHCO$_3$ solution (130 m≙30 V) and again with water (270 ml≙60V). The solid was dried under vacuum at 35° C.

Output: 4.0 g; Yield: 65.1%; Purity 79.25%.

CDEG:

20% piperidine in DMF (25 ml≙5 V) was charged into an RBF under a nitrogen atmosphere. The solution was cooled to −5° C. and CDEG-1 (5.0 g) was added. The reaction mixture was stirred for 45 minutes at 0° C. The reaction mixture was poured into DIPE (250 ml≙50 V) and then stirred for 15 minutes. The precipitated solid was filtered off under nitrogen and washed with DIPE (50 ml≙10 V). The solid was then taken up in ethyl acetate (125 ml≙25 V) and stirred for 1 hr at 25° C. The fine solid obtained was filtered, washed with ethyl acetate (50 ml≙10 V), and then dried under vacuum.

Output: 4.7 g; Yield: Quantitative, Purity: 87.6%, D-Ser impurity 1.5%, hydantoin impurity 0.16%.

HPLC Condition for CDEG:

Column: YMC basic (250 mm×3.0 mm), 5μ

Mobile phase A: 0.1% TFA in ACN

Mobile phase B: 0.1% TFA in H$_2$O

Wave length: 226 nm, Diluent: Mobile phase A: M.P.B=27:73

Column tem: 50° C., inject.vol. 50 μl

Gradient T/% A=0/73, 18/70, 41/30, 43/73, 50/73

Flow rate 0.5 ml/min

The invention claimed is:

1. A liquid-phase process for preparing Degarelix having the formula Ac-AA$_1$-AA$_{10}$-NH$_2$:

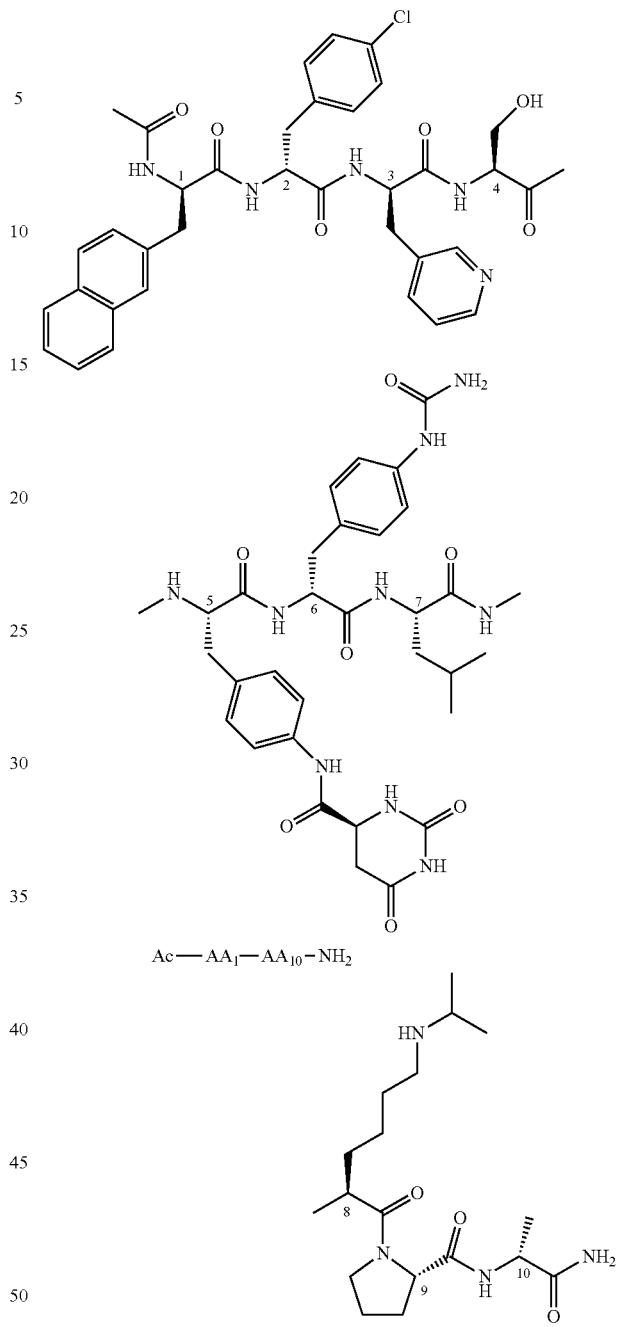

or a pharmaceutically acceptable salt or solvate thereof; comprising the steps of:
coupling peptides (P$_4$)Ac-AA$_1$-AA$_4$ with (Pε)AA$_5$-AA$_{10}$NH$_2$ or coupling peptides Ac-AA$_1$-AA$_3$ with (P$_4$)(Pε)AA$_4$-AA$_{10}$NH$_2$ in an organic solvent,
wherein the organic solvent comprises the two peptides, a peptide coupling reagent and an organic amine base dissolved therein,
wherein Pε is an ε-amino protecting group and P4 is a hydroxyl protecting group or hydrogen, wherein the peptide coupling agent in the case of coupling (P$_4$)Ac-AA$_1$-AA$_4$ with (Pε)AA$_5$-AA$_{10}$NH$_2$ is selected from at least one of o-(7-azabenzotriazol-1-yl)-1,1,3,3-tetramethyluronium hexafluorophosphate (HATU) and 2-(benzotriazol-1-yl)oxy-1,3-dimethylimidazolidinium hexfluorophosphate (BOP), and
wherein the peptides have the following formulae:
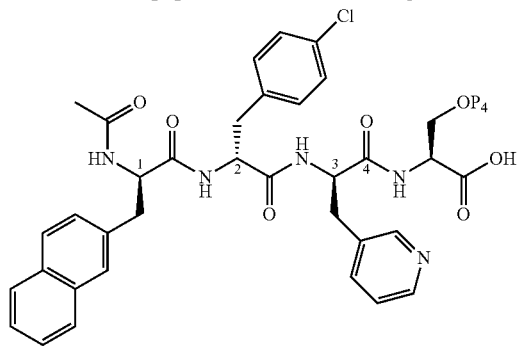
(P₄)Ac—AA₁—AA₄
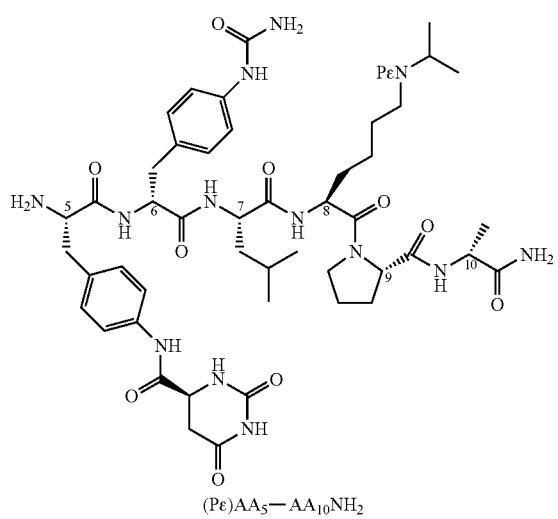
(Pε)AA₅—AA₁₀NH₂
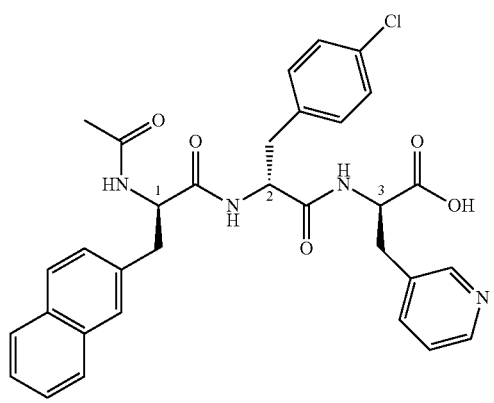
Ac—AA₁—AA₃
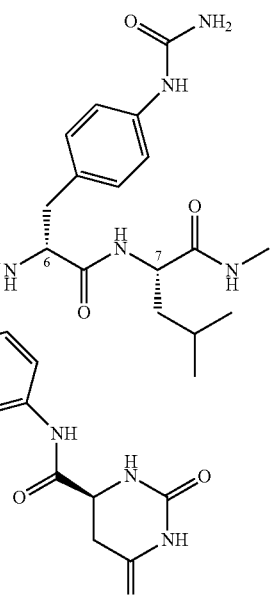
(P₄)(Pε)AA₄—AA₁₀NH₂
to provide a protected Degarelix precursor having the formula (P₄)(Pε)Ac-AA₁-AA₁₀-NH₂:

-continued

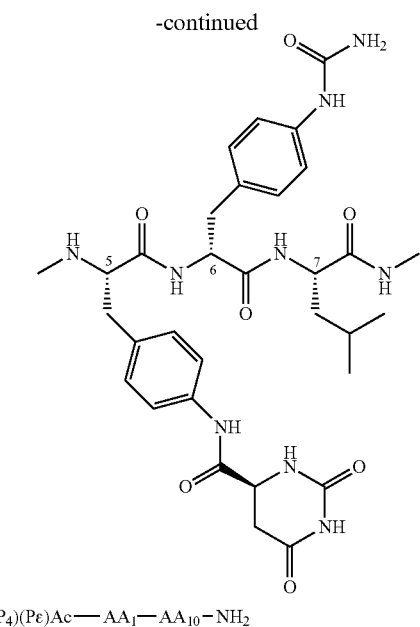

(P₄)(Pε)Ac—AA₁—AA₁₀–NH₂

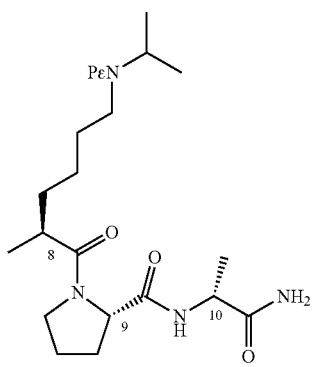

and
cleaving the ε-amino protecting group Pε from the Degarelix precursor in an organic solvent, wherein the organic solvent comprises the precursor and a cleaving agent dissolved therein to provide Degarelix.

2. The process according to claim 1, wherein the cleaving agent is chosen from trifluoroacetic acid and piperidine.

3. The process according to claim 1, wherein Pε is chosen from t-butoxycarbonyl (Boc), 9-fluorenylmethyloxycarbonyl (Fmoc) and allyloxycarbonyl (Alloc).

4. The process according to claim 1, wherein the Pε protecting group is Fmoc.

5. The process according to claim 1, wherein the organic solvent is DMF.

6. The process according to claim 1, wherein in the case of coupling Ac-AA₁-AA₃ with P₄)(Pε)AA₄-AA₁₀NH₂, the peptide coupling reagent is chosen from at least one of o-(7-azabenzotriazol-1-yl)-1,1,3,3-tetramethyluronium hexafluorophosphate (HATU), o-(benzotriazol-1-yl)-1,1,3,3-tetramethyluronium hexafluorophosphate (HBTU) and o-(benzotriazol-1-yl)-1,1,3,3-tetramethyluronium tetrafluoroborate (TBTU), and 1-ethyl-3-(3-dimethylaminopropyl) carbodiimide hydrochlroride (EDC.HCl), (2-(6-chloro-1-H-benzotriazol-1-yl)-1,1,3,3-tetramethylaminium) hexafluorophosphate (HCTU), 2-(benzotriazol-1-yl)oxy-1,3-dimethylimidazolidinium hexfluorophosphate (BOP), and diisopropylcarbodiimide (DIC).

7. The process according to claim 1, wherein the organic amine base is chosen from at least one of N,N'-diisopropyl ethyl amine (DIPEA), N-methylmorpholine (NMM), triethyl amine (TEA) and 2,4,6-trimethylpyridine.

8. The process according to claim 1, wherein the solution further comprises a coupling additive chosen from 3,4-dihydro-3-hydroxy4-oxo-1,2,3-benzotriazine (HOOBt), 1-hydroxy-7-aza-benzotriazole (HOAt) and 1-hydroxybenzotriazole (HOBt) dissolved therein.

9. The process according to claim 1, wherein the organic amine base is DIPEA and the peptide coupling reagent is HATU.

10. The process according to claim 8, wherein the organic amine base is DIPEA and the peptide coupling additive is HOAt.

11. The process according to claim 8, wherein the peptide coupling reagent is HATU and the peptide coupling additive is HOAt.

12. The process according to claim 8, wherein the organic amine base is DIPEA, the peptide coupling reagent is HATU and the peptide coupling additive is HOAt.

13. The process according to claim 1, wherein the organic amine base is used in an amount ranging from about 2.5 to about 3.5 molar equivalents of AA₅-AA₁₀ hexapeptide.

14. The process according to claim 1, wherein the organic solvent is cooled to a temperature of −10° C. or lower and the coupling reaction is then performed at that temperature.

15. The process according to claim 8, wherein the peptides and coupling additive are first dissolved in the organic solvent before adding the coupling reagent and the organic amine.

16. A liquid-phase process for preparing a Degarelix intermediate having the formula (P₄)Ac-AA₁-AA₄:

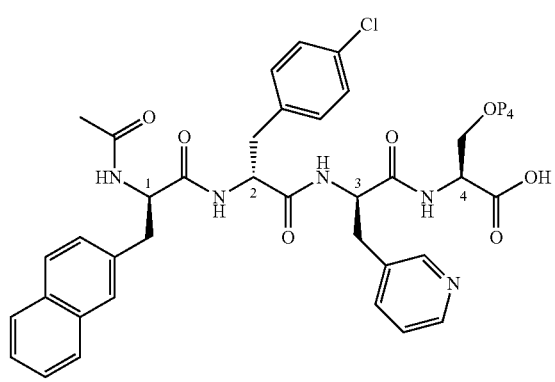

(P₄)Ac—AA₁—AA₄ or a pharmaceutically acceptable salt or solvate thereof,
comprising the step of hydrolyzing a compound having the formula (P₄)Ac-AA₁-AA₄-R with an alkaline hydroxide, wherein R is a carboxyl protecting group, and P₄ is hydrogen or a hydroxyl protecting group, wherein the compound (P₄)Ac-AA₁-AA₄-R has the formula:

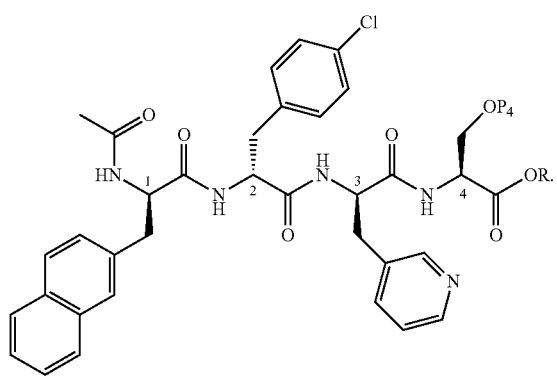

(P4)Ac—AA1—AA4—R

17. A liquid-phase process for preparing a hexapeptide (Pε)AA5-AA10NH2 comprising:

coupling (Pε)AA6-AA10NH2 and (PX)AA5, wherein PX is an amino protecting group, AA5 is 4Aph(L-Hor), AA6 is D-Aph(Cbm), AA7 is Leu, AA8 is Lys(iPr), AA9 is Pro, AA10 is D-Ala, and Pε is an ε-amino protecting group, to provide (PX)(Pε)AA5-AA10NH2, and cleaving Px with TFA to provide (Pε)AA5-AA10NH2, wherein (PX)(Pε)AA5-AA10NH2, (Pε)AA6-AA10NH2 and (PX)AA5 have the following structures:

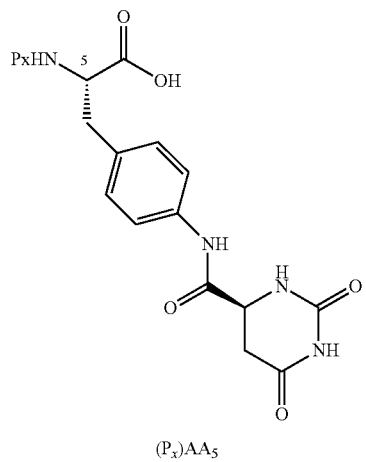

(PX)AA5

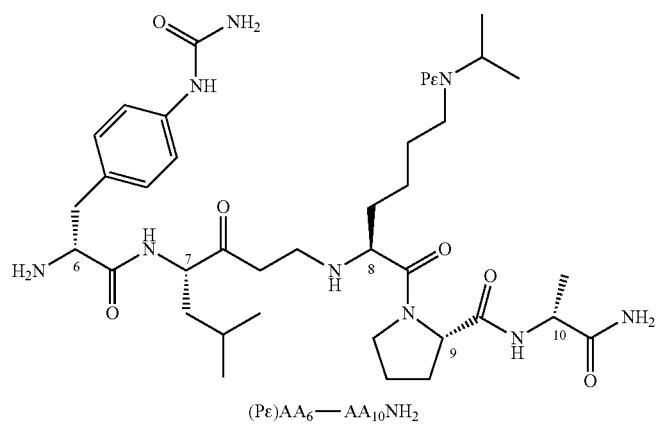

(Pε)AA6—AA10NH2

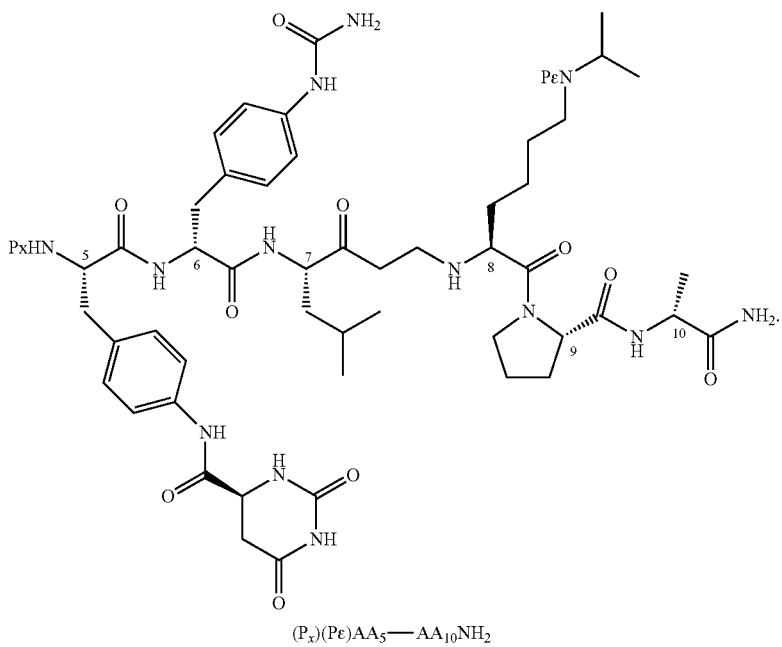

(P$_x$)(Pε)AA$_5$—AA$_{10}$NH$_2$

18. The process according to claim 16, wherein the compound having the formula Ac-AA$_1$-AA$_4$-R is first prepared by coupling Ac-AA$_1$-AA$_3$ with (P$_4$)AA$_4$-R or coupling Ac-AA$_1$-AA$_2$ with (P$_4$)AA$_3$-AA$_4$-R, the peptides having the following formulae:

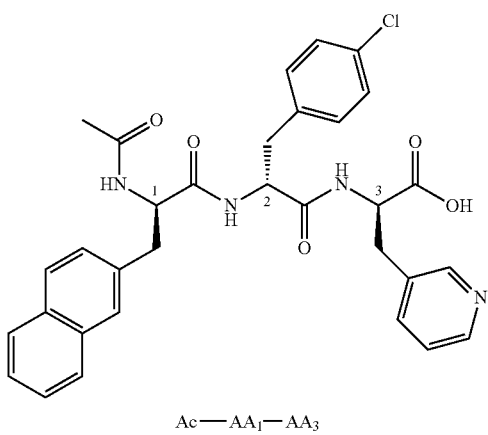

Ac—AA$_1$—AA$_3$

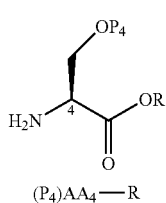

(P$_4$)AA$_4$—R

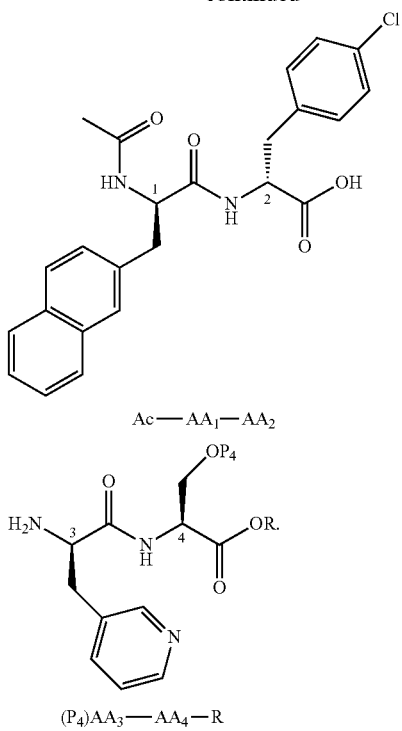

Ac—AA$_1$—AA$_2$ (P$_4$)AA$_3$—AA$_4$—R

19. The process according to claim 16, wherein R is methyl or benzyl.

20. The process according to claim 16, wherein the alkaline hydroxide is LiOH.

21. Intermediate polypeptides according to the formulae:
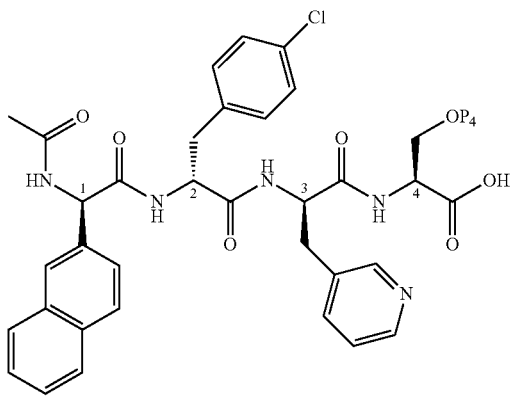
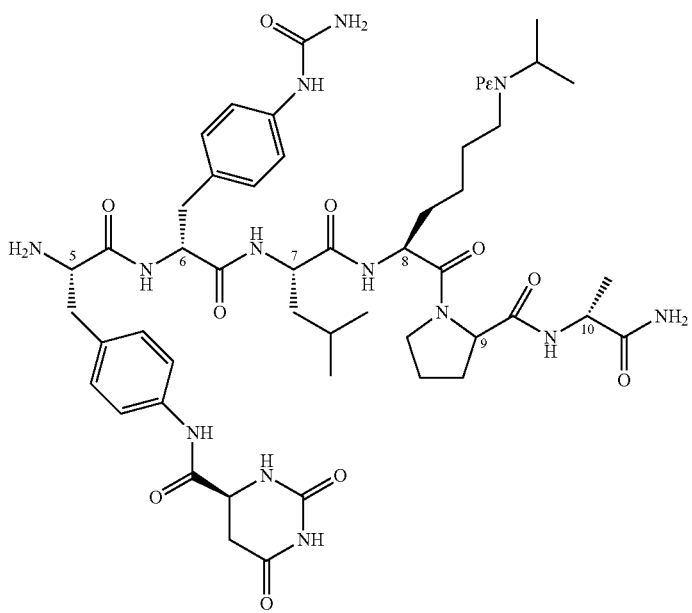
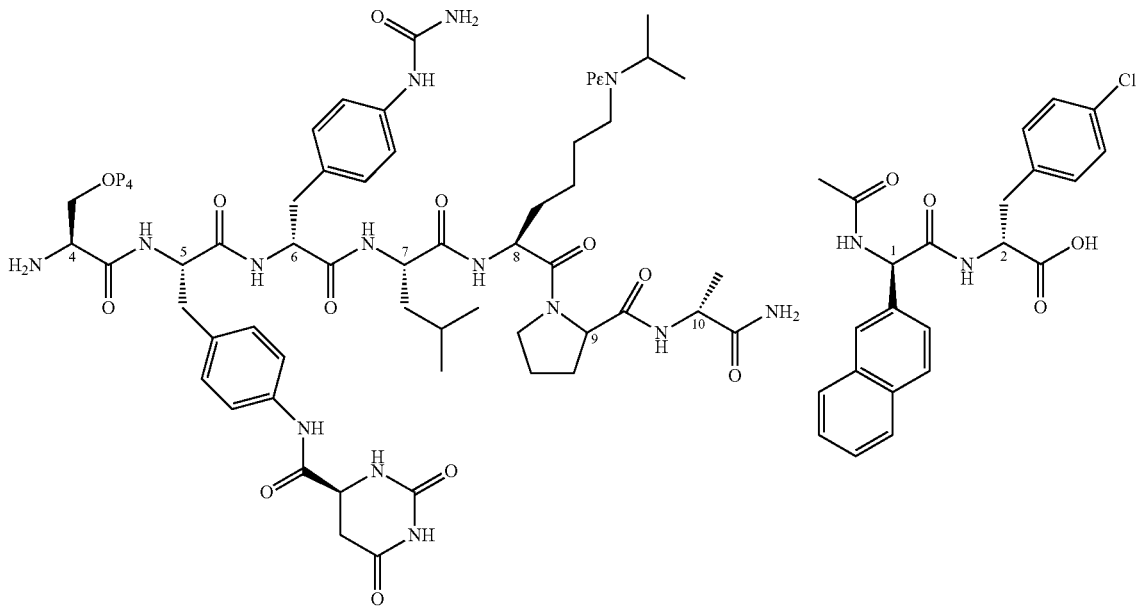

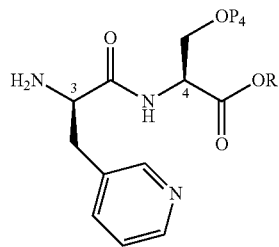

wherein R is a carboxyl protecting group, Pε is an amino protecting group, and P4 is hydrogen or a hydroxyl protecting group.

22. A solid-phase process for preparing a Degarelix intermediate having the formula (P4)Ac-AA$_1$-AA$_4$:

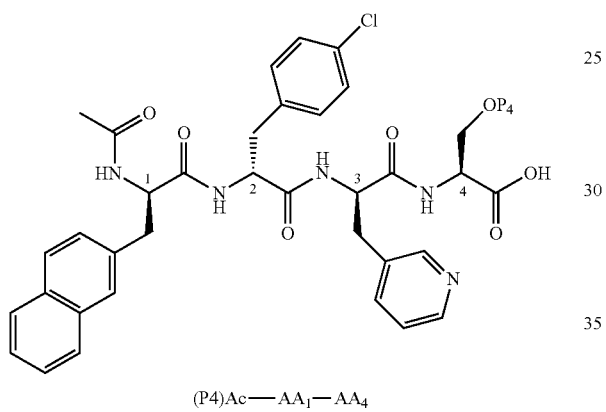

(P4)Ac—AA$_1$—AA$_4$ or a pharmaceutically acceptable salt or solvate thereof, comprising the steps:

a) reacting (PN)AA$_2$ with

(P4)AA$_3$—AA$_4$—RESIN to provide

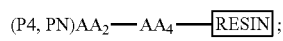

(P4, PN)AA$_2$—AA$_4$—RESIN;

b) removal of PN from

(P4, PN)AA$_2$—AA$_4$—RESIN to provide

(P4)AA$_2$—AA$_4$—RESIN;

c) reacting (PN)AA1 with

(P4)AA$_2$—AA$_4$—RESIN to provide

(P4, PN)AA$_1$—AA$_4$—RESIN;

d) if PN is not acetyl, removal of PN from

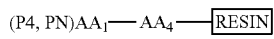

(P4, PN)AA$_1$—AA$_4$—RESIN to provide

(P4)AA$_1$—AA$_4$—RESIN and subsequently acetylating

(P4)AA$_1$—AA$_4$—RESIN to provide

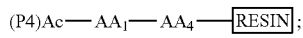

(P4)Ac—AA$_1$—AA$_4$—RESIN;

and
e) cleaving

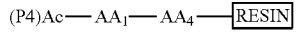

(P4)Ac—AA$_1$—AA$_4$—RESIN to provide (P4)Ac-AA$_1$-AA$_4$,
wherein P4 is H or a hydroxyl protecting group on AA$_4$, and PN is an amino protecting group.

23. A liquid-phase process for preparing a hexapeptide (Pε)AA$_5$-AA$_{10}$NH$_2$ comprising:
coupling (P5)AA$_5$-AA$_7$ with (Pε)AA$_8$-AA$_{10}$NH$_2$ to provide (P5, Pε)AA$_5$-AA$_{10}$NH$_2$, and
subsequently cleaving P5 to provide (Pε)AA$_5$-AA$_{10}$NH$_2$, wherein P5 is an amino-protecting group on AA$_5$ and Pε is a side chain amino protecting group on AA$_6$ and wherein $AA_5$ is 4Aph(L-Hor), $AA_6$ is D-Aph(Cbm), $AA_7$ is Leu, $AA_8$ is Lys(iPr), $AA_9$ is Pro, and $AA_{10}$ is D-Ala.

24. The liquid-phase process of claim 23, followed by coupling (P4)Ac-$AA_1$-$AA_4$ to (Pε)$AA_5$-$AA_{10}NH_2$.

25. The process according to claim 16, wherein the carboxyl protecting group is chosen from a $C_1$-$C_4$ alkyl and benzyl group.

26. The polypeptide according to claim 21, wherein the carboxyl protecting group is chosen from a $C_1$-$C_4$ alkyl and benzyl group.

* * * * *